(12) United States Patent
Fukushima et al.

(10) Patent No.: US 11,129,682 B2
(45) Date of Patent: Sep. 28, 2021

(54) MEDICAL ROBOT ARM APPARATUS, MEDICAL ROBOT ARM CONTROL SYSTEM, MEDICAL ROBOT ARM CONTROL METHOD, AND PROGRAM

(71) Applicant: SONY OLYMPUS MEDICAL SOLUTIONS INC., Tokyo (JP)

(72) Inventors: Tetsuharu Fukushima, Tokyo (JP); Wataru Kokubo, Tokyo (JP); Toshimitsu Tsuboi, Tokyo (JP); Atsushi Miyamoto, Kanagawa (JP); Kenichiro Nagasaka, Tokyo (JP); Kenji Hirose, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 128 days.

(21) Appl. No.: 14/800,418

(22) Filed: Jul. 15, 2015

(65) Prior Publication Data
US 2015/0313679 A1 Nov. 5, 2015

Related U.S. Application Data

(63) Continuation-in-part of application No. PCT/JP2014/074917, filed on Sep. 19, 2014.

(30) Foreign Application Priority Data

Sep. 24, 2013 (JP) .............................. JP2013-197003

(51) Int. Cl.
*A61B 1/04* (2006.01)
*A61B 1/00* (2006.01)
(Continued)

(52) U.S. Cl.
CPC ................ *A61B 34/30* (2016.02); *A61B 1/04* (2013.01); *A61B 90/06* (2016.02); *A61B 90/361* (2016.02);
(Continued)

(58) Field of Classification Search
CPC ....... A61B 34/30; A61B 90/06; A61B 90/361; A61B 1/04; A61B 1/00149;
(Continued)

(56) References Cited

U.S. PATENT DOCUMENTS 5,231,279 A 7/1993 Nakamura
6,120,433 A 9/2000 Mizuno et al.
(Continued)

FOREIGN PATENT DOCUMENTS

JP 61-224012 A 10/1986
JP 5-173053 A 7/1993
(Continued)

OTHER PUBLICATIONS

Extended European Search Report dated Mar. 15, 2017 in Patent Application No. 14849594.8.
(Continued)

*Primary Examiner* — Michael J Carey
*Assistant Examiner* — Genja M Frankert
(74) *Attorney, Agent, or Firm* — Xsensus LLP

(57) ABSTRACT

Provided is a surgical imaging apparatus that includes a multi-link, multi joint structure including a plurality of joints that interconnect a plurality of links to provide the multi-link, multi joint structure with a plurality of degrees of freedom, at least one video camera being disposed on a distal end of the multi-link, multi-joint structure; at least one actuator that drives at least one of the plurality of joints; and circuitry that detects a joint force experienced at the at least one of the plurality of joints in response to an applied external force, and controls the at least one actuator based on the joint force so as to position the video camera.

32 Claims, 11 Drawing Sheets

(51) Int. Cl.
*A61B 34/30* (2016.01)
*B25J 9/16* (2006.01)
*G05B 15/02* (2006.01)
*A61B 90/00* (2016.01)

(52) U.S. Cl.
CPC ........... *B25J 9/1633* (2013.01); *B25J 9/1697* (2013.01); *G05B 15/02* (2013.01); *A61B 1/00149* (2013.01); *A61B 2090/064* (2016.02); *A61B 2090/066* (2016.02); *G05B 2219/39237* (2013.01); *G05B 2219/40599* (2013.01); *G05B 2219/40613* (2013.01); *G05B 2219/41397* (2013.01)

(58) Field of Classification Search
CPC ......... A61B 2090/066; A61B 2090/064; B25J 9/1697; B25J 9/1633; G05B 15/02; G05B 2219/39237; G05B 2219/41397; G05B 2219/40613; G05B 2219/40599
See application file for complete search history.

(56) References Cited

U.S. PATENT DOCUMENTS

| | | | |
|---|---|---|---|
| 7,646,161 | B2 | 1/2010 | Alin Albu-Schäffer et al. |
| 2001/0025183 | A1* | 9/2001 | Shahidi ................. A61B 90/10 606/130 |
| 2004/0034282 | A1* | 2/2004 | Quaid, III ............. A61B 34/20 600/300 |
| 2006/0142657 | A1 | 6/2006 | Quaid et al. |
| 2007/0013336 | A1 | 1/2007 | Nowlin et al. |
| 2007/0014567 | A1* | 1/2007 | Rossner ................. A61B 90/35 396/429 |
| 2007/0083098 | A1* | 4/2007 | Stern ................... A61B 1/00188 600/407 |
| 2007/0142751 | A1 | 6/2007 | Kang et al. |
| 2007/0142823 | A1* | 6/2007 | Prisco .................... B25J 9/1638 606/1 |
| 2007/0287992 | A1* | 12/2007 | Diolaiti ................. G05B 19/19 606/1 |
| 2009/0000626 | A1 | 1/2009 | Quaid et al. |
| 2009/0000627 | A1 | 1/2009 | Quaid et al. |
| 2009/0012531 | A1 | 1/2009 | Quaid et al. |
| 2009/0012532 | A1 | 1/2009 | Quaid et al. |
| 2009/0105878 | A1 | 4/2009 | Nagasaka |
| 2009/0248036 | A1* | 10/2009 | Hoffman ................. A61B 1/045 606/130 |
| 2009/0326322 | A1* | 12/2009 | Diolaiti .............. A61B 1/00039 600/112 |
| 2010/0094312 | A1* | 4/2010 | Ruiz Morales ........ B25J 13/085 606/130 |
| 2010/0206651 | A1* | 8/2010 | Nagasaka ................ B25J 5/007 180/218 |
| 2010/0318224 | A1* | 12/2010 | Okuda ................... B25J 9/1676 700/255 |
| 2011/0245844 | A1* | 10/2011 | Jinno ..................... A61B 34/71 606/130 |
| 2011/0264108 | A1 | 10/2011 | Nowlin et al. |
| 2011/0264109 | A1 | 10/2011 | Nowlin et al. |
| 2011/0264110 | A1 | 10/2011 | Nowlin et al. |
| 2011/0264111 | A1 | 10/2011 | Nowlin et al. |
| 2011/0264112 | A1 | 10/2011 | Nowlin et al. |
| 2011/0270271 | A1 | 11/2011 | Nowlin et al. |
| 2011/0276059 | A1 | 11/2011 | Nowlin et al. |
| 2011/0282358 | A1* | 11/2011 | Gomez .............. A61B 17/3423 606/130 |
| 2012/0107984 | A1* | 5/2012 | Oh .................... H01L 21/02422 438/34 |
| 2012/0109150 | A1 | 5/2012 | Quaid et al. |
| 2012/0182134 | A1* | 7/2012 | Doyle ................. A61B 1/00149 340/12.22 |
| 2013/0041226 | A1* | 2/2013 | McDowall ......... A61B 1/00009 600/166 |
| 2013/0068017 | A1* | 3/2013 | Perkins ................... G01P 15/18 73/504.02 |
| 2013/0128110 | A1* | 5/2013 | Jannard ................ H04N 5/2252 348/375 |
| 2013/0215372 | A1* | 8/2013 | Oke ....................... G02F 1/1345 349/149 |
| 2013/0265462 | A1* | 10/2013 | Kano .................. H04N 5/23229 348/223.1 |
| 2015/0032126 | A1 | 1/2015 | Nowlin et al. |
| 2015/0051733 | A1 | 2/2015 | Nowlin et al. |

FOREIGN PATENT DOCUMENTS

| | | | |
|---|---|---|---|
| JP | 8-117238 | A | 5/1996 |
| JP | 9-201329 | A | 8/1997 |
| JP | 10-231100 | A | 9/1998 |
| JP | 2008-538184 | A | 10/2008 |
| WO | WO 2006/091494 | A1 | 8/2006 |
| WO | WO 2006/124390 | A2 | 11/2006 |

OTHER PUBLICATIONS

Ken'ichiro Nagasaka et al., "Whole-body Cooperative Force Control for a Two-Armed and Two-Wheeled Mobile Robot Using Generalized Inverse Dynamics and Idealized Joint Units", 2010 IEEE International Conference on Robotics and Automation, ICRA 2010, XP031743409, May 3-8, 2010, pp. 3377-3383.

International Search Report dated Dec. 16, 2014 in PCT/JP2014/074917.

Ken'ichiro Nagasaka, et al., "The Application of Generalized Inverse Dynamics to the Robot Equipped with Idealized Joint Units", Robotics Symposia Yokoshu, vol. 14, The Robotics Society of Japan, Mar. 16, 2009, pp. 1-7.

Japanese Office Action dated May 30, 2017 in Patent Application No. 2015-539173 (with English Translation).

Office Action dated Dec. 4, 2017, in the People's Republic of China Patent Application No. 2014800514272 (with English-language translation).

Office Action dated Oct. 23, 2018 in Japanese Patent Application No. 2018-000045 (with English language translation).

Japanese Office Action dated Jun. 4, 2019 in Japanese Application No. 2018-000045.

* cited by examiner

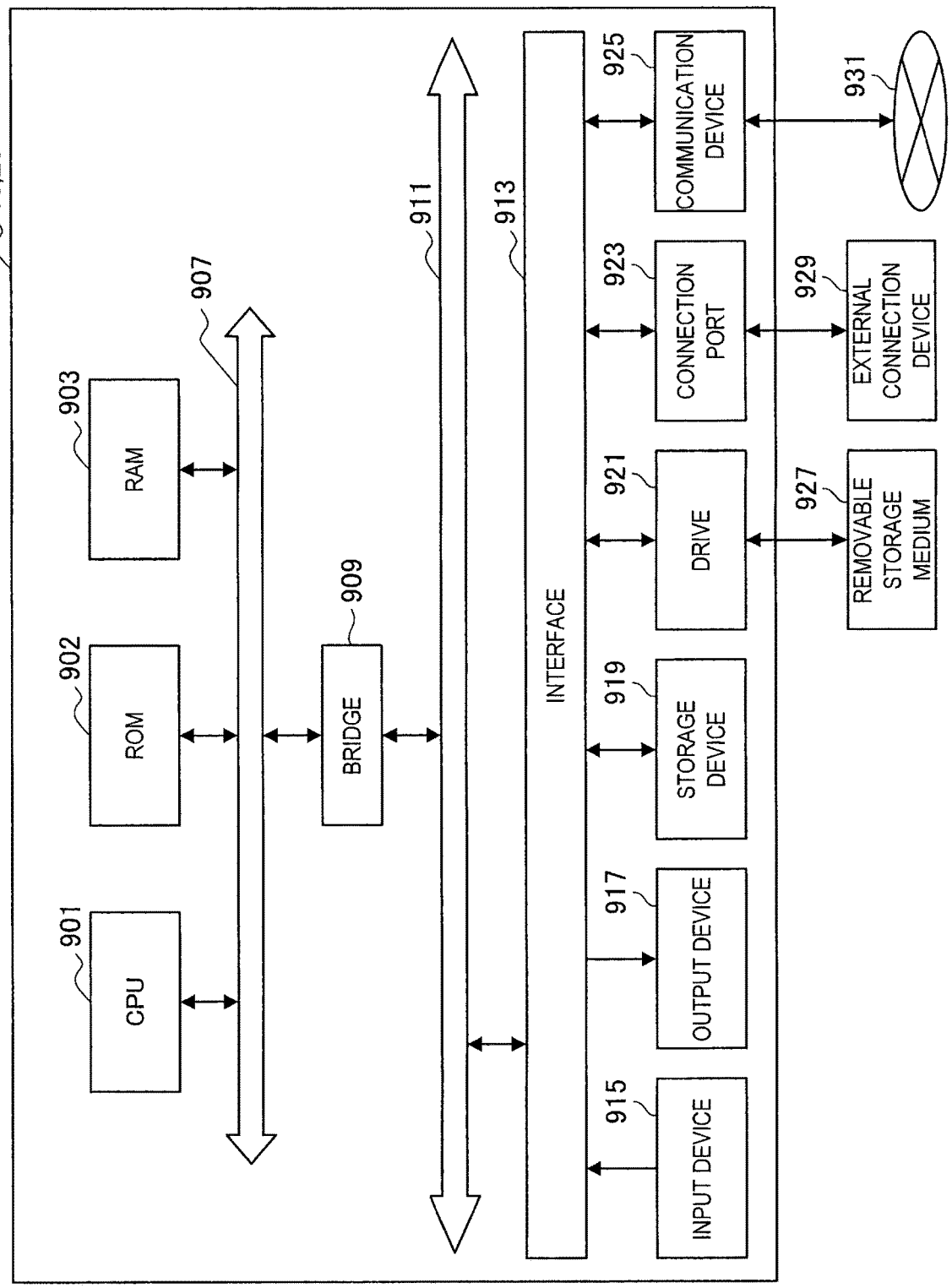

MEDICAL ROBOT ARM APPARATUS, MEDICAL ROBOT ARM CONTROL SYSTEM, MEDICAL ROBOT ARM CONTROL METHOD, AND PROGRAM

CROSS-REFERENCE TO RELATED APPLICATIONS

This application is a Continuation-In-Part Application of PCT Application No. PCT/JP2014/074917, filed Sep. 19, 2014, which claims priority to Japanese Patent Application No. 2013-197003, filed Sep. 24, 2013.

TECHNICAL FIELD

The present disclosure relates to a medical robot arm apparatus, a medical robot arm control system, a medical robot arm control method, and a program.

BACKGROUND ART

In recent years, in the medical field and the industrial field, robot apparatuses have been widely used in order to perform tasks faster with a high degree of accuracy. Commonly, a robot apparatus is a multi-link structure in which a plurality of links are connected with one another by joint units, and as rotary driving in the plurality of joint units is controlled, driving of the whole robot apparatus is controlled.

Here, position control and force control are known as control methods of the robot apparatus and each of the joint units. In position control, for example, a command value such as an angle is provided to an actuator of a joint unit, and driving of the joint unit is controlled according to the command value. Meanwhile, in force control, a target value of force applied to a task target by a whole robot apparatus is given, and driving of a joint unit (for example, torque generated by the joint unit) is controlled such that the force indicated by the target value is implemented.

Generally, most robot apparatuses are driven by position control since it is convenient to control and a system configuration is simple. However, position control is commonly called "hard control" since cannot easily deal with external force flexibly, and position control is not suitable for a robot apparatus performing a task (purpose of motion) while performing physical interaction (for example, physical interaction with a person) with various external worlds. Meanwhile, force control has a complicated system configuration, but can implement "soft control" of a power order, and thus force control is a control method suitable, particularly, for a robot apparatus performing physical interaction with a person and a control method having excellent usability.

For example, as a robot apparatus to which force control is applied, Patent Literature 1 discloses a robot apparatus that includes a movement mechanism configured with 2 wheels and an arm unit configured with a plurality of joint units, and performs control such that the wheels and the joint units are driven in a cooperative manner as a whole (performs whole body cooperative control).

Further, in force control, it is necessary to detect torque (including generated torque generated by a joint unit and external torque given from the outside to the joint unit) with a high degree of accuracy in each joint unit of a robot apparatus, and perform feedback control and/or feedforward control. For example, Patent Literature 2 discloses a torque sensor that includes a decoupling structure, and performs high-accuracy torque detection in which influence of vibration is reduced as much as possible.

CITATION LIST

Patent Literature

Patent Literature 1: JP 2010-188471A
Patent Literature 2: JP 2011-209099A

SUMMARY

Technical Problem

Meanwhile, in recent years, in the medical field, attempts to use a balance arm in which various medical units (front edge units) are installed at a front edge of an arm unit when various medical procedures (for example, surgery or an examination) are performed have been made. For example, a method in which a unit with various imaging functions such as a microscope, an endoscope, or an imaging unit (camera) is installed on a front edge of an arm unit of a balance arm as a front edge unit, and a practitioner (a user) performs various medical procedures while observing an image of an affected area captured by the front edge unit has been proposed. However, the balance arm has to be equipped with a counter balance weight (also called a counter weight or a balancer) for maintaining balance of force when the arm unit is moved and thus a device size tends to increase. A device used in a medical procedure has to be small in size since it is necessary to secure a task space for the medical procedure, but it is difficult to meet such a demand in general balance arms being proposed. Further, in the balance arm, only some driving of the arm unit, for example, only biaxial driving for moving the front edge unit on a (two-dimensional) plane is electric driving, and manual positioning by the practitioner or a medical staff therearound is necessary for movement of the arm unit and the front edge unit. Thus, in the general balance arms, it is difficult to secure stability (for example, positioning accuracy of the front edge unit, vibration suppression, and the like) at the time of photography and secure a degree of freedom of photography by which it is possible to photograph in various directions, for example, in a state in which a certain part of a patient's body is fixed as a part to be photographed.

In light of such a situation, medical robot arm apparatuses in which driving is controlled by position control have been proposed as devices to take the place of balance arms. However, in order to more efficiently perform a medical procedure and reduce a burden on a user, high operability enabling more intuitive control of a position or posture of an arm unit and a front edge unit by a user is necessary for driving control of a robot arm apparatus. In a robot arm apparatus in which driving is controlled by position control, it is difficult to meet such a user demand.

In light of the foregoing, it is desirable to perform a medical procedure efficiently and reduce a burden on a user during the medical procedure by implementing a medical robot arm apparatus capable of performing driving control of a front edge unit and an arm unit having high stability and a high degree of freedom of operability. In this regard, the present disclosure provides a medical robot arm apparatus, a medical robot arm control system, a medical robot arm control method, and a program, which are novel and improved and capable of further improving user convenience and further reducing a burden on a user.

Solution to Problem

According to an embodiment of the present disclosure, there is provided a medical robot arm apparatus including a plurality of joint units configured to connect a plurality of links and implement at least 6 or more degrees of freedom in driving of a multi-link structure configured with the plurality of links, and a drive control unit configured to control driving of the joint units based on states of the joint units. A front edge unit attached to a front edge of the multi-link structure is at least one medical apparatus.

According to another embodiment of the present disclosure, there is provided a medical robot arm control system including a medical robot arm apparatus including a plurality of joint units configured to connect a plurality of links and implement at least 6 or more degrees of freedom with respect to a multi-link structure configured with the plurality of links and a drive control unit that controls driving of the joint units based on detected states of the plurality of joint units, and a control device including a whole body cooperative control unit configured to calculate a control value for whole body cooperative control of the multi-link structure according to generalized inverse dynamics using a state of the multi-link structure acquired based on the detected states of the plurality of joint units and a purpose of motion and a constraint condition of the multi-link structure. A front edge unit attached to a front edge of the multi-link structure is at least one medical apparatus.

According to another embodiment of the present disclosure, there is provided a medical robot arm control method including detecting states of a plurality of joint units configured to connect a plurality of links and implement at least 6 or more degrees of freedom with respect to a multi-link structure configured with the plurality of links, and controlling driving of the joint units based on the detected states of the plurality of joint units. A front edge unit attached to a front edge of the multi-link structure is at least one medical apparatus.

According to another embodiment of the present disclosure, there is provided a program for causing a computer to execute a function of detecting states of a plurality of joint units configured to connect a plurality of links and implement at least 6 or more degrees of freedom with respect to a multi-link structure configured with the plurality of links, and a function of controlling driving of the joint units based on the detected states of the plurality of joint units. A front edge unit attached to a front edge of the multi-link structure is at least one medical apparatus.

According to the present disclosure, an arm unit having a multi-link structure in a robot arm apparatus has at least 6 or more degrees of freedom, and driving of each of a plurality of joint units configuring the arm unit is controlled by a drive control unit. Further, a medical apparatus is installed at a front edge of the arm unit. As driving of each joint unit is controlled as described above, driving control of the arm unit having a high degree of freedom is implemented, and a medical robot arm apparatus having high operability for a user is implemented.

Advantageous Effects of Disclosure

As described above, according to the present disclosure, it is possible to further improve user convenience and further reduce a burden on a user.

BRIEF DESCRIPTION OF DRAWINGS

FIG. 11 is a functional block diagram illustrating an exemplary configuration of a hardware configuration of a robot arm apparatus and a control device according to an embodiment of the present disclosure and.

DESCRIPTION OF EMBODIMENTS

Figure 1:
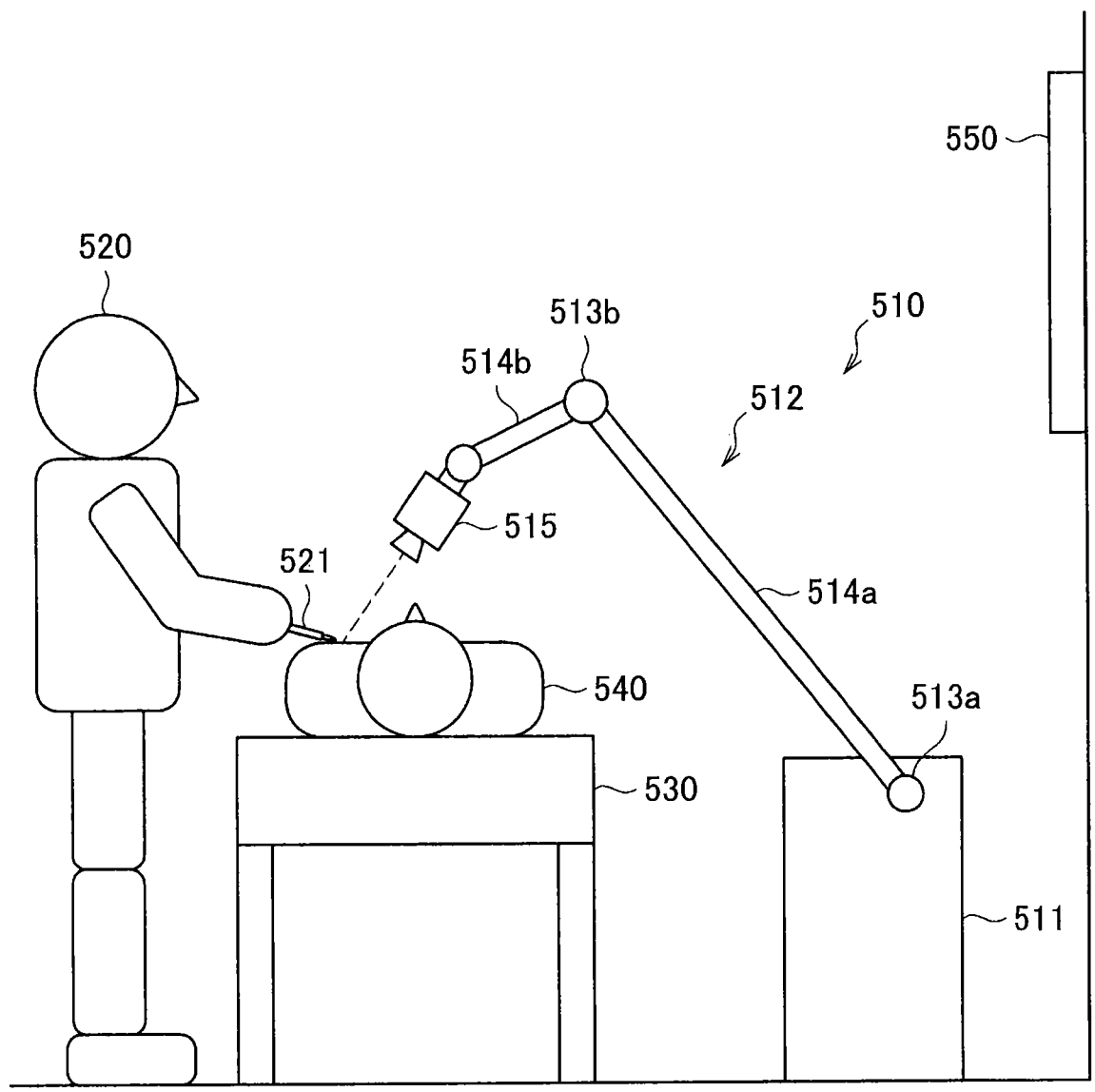
FIG. 1 is an explanatory diagram for describing an application example of using a robot arm apparatus according to an embodiment of the present disclosure for a medical purpose.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will proceed in the following order.
1. Review of medical robot arm apparatus
2. Embodiment of present disclosure
2-1. External appearance of robot arm apparatus
2-2. Generalized inverse dynamics
2-2-1. Virtual force calculating process
2-2-1. Actual force calculating process
2-3. Ideal joint control
2-4. Configuration of robot arm control system
2-5. Specific example of purpose of motion
3. Processing procedure of robot arm control method
4. Hardware configuration
5. Conclusion

<1. Review of Medical Robot Arm Apparatus>

First, the background in which the inventors have developed the present disclosure will be described in order to further clarify the present disclosure.

An application example of using a robot arm apparatus according to an embodiment of the present disclosure for a medical purpose will be described with reference to FIG. 1. FIG. 1 is an explanatory diagram for describing an application example of using a robot arm apparatus according to an embodiment of the present disclosure for a medical purpose.

FIG. 1 schematically illustrates an exemplary medical procedure using the robot arm apparatus according to the present embodiment. Specifically, FIG. 1 illustrates an example in which a doctor serving as a practitioner (user) 520 performs surgery on a medical procedure target (patient) 540 on a medical procedure table 530, for example, using surgical instruments 521 such as a scalpel, tweezers, and forceps. In the following description, the medical procedure refers to a general concept including various kinds of medical treatments that the doctor serving as the user 520 performs on the patient of the medical procedure target 540 such as surgery or an examination. The example of FIG. 1 illustrates surgery as an example of the medical procedure, but the medical procedure using a robot arm apparatus 510 is not limited to surgery and may be various kinds of other medical procedures such as an examination using an endoscope.

The robot arm apparatus 510 according to the present embodiment is installed at the side of the medical procedure table 530. The robot arm apparatus 510 includes a base unit 511 serving as a base and an arm unit 512 extending from the base unit 511. The arm unit 512 includes a plurality of joint units 513a, 513b, 513c, a plurality of links 514a and 514b connected by the joint units 513a and 513b, and an imaging unit 515 installed at the front edge of the arm unit 512. In the example illustrated in FIG. 1, for the sake of simplification, the arm unit 512 includes the 3 joint units 513a to 513c and the 2 links 514a and 514b, but practically, for example, the number and the shape of the joint units 513a to 513c and the links 514a and 514b and a direction of the driving shaft of the joint units 513a to 513c may be appropriately set to express a desired degree of freedom in view of a degree of freedom of the position and posture of the arm unit 512 and the imaging unit 515.

The joint units 513a to 513c have a function of connecting the links 514a and 514b to be rotatable, and as the joint units 513a to 513c are rotationally driven, driving of the arm unit 512 is controlled. Here, in the following description, the position of each component of the robot arm apparatus 510 is the position (coordinates) in a space specified for driving control, and the posture of each component is a direction (angle) to an arbitrary axis in a space specified for driving control. Further, in the following description, driving (or driving control) of the arm unit 512 refers to changing (controlling a change of) the position and posture of each component of the arm unit 512 by performing driving (or driving control) of the joint units 513a to 513c and driving (or driving control) of the joint units 513a to 513c.

Various kinds of medical apparatuses are connected to the front edge of the arm unit 512 as the front edge unit. In the example illustrated in FIG. 1, the imaging unit 515 is installed at the front edge of the arm unit 512 as an exemplary front edge unit. The imaging unit 515 is a unit that acquires an image (a photographed image) of a photographing target and is, for example, a camera capable of capturing a moving image or a still image. As illustrated in FIG. 1, the posture or the position of the arm unit 512 and the imaging unit 515 is controlled by the robot arm apparatus 510 such that the imaging unit 515 installed at the front edge of the arm unit 512 photographs a state of a medical procedure part of the medical procedure target 540. The front edge unit installed at the front edge of the arm unit 512 is not limited to the imaging unit 515 and may be various kinds of medical apparatuses. For example, the medical apparatus includes various kinds of units used when the medical procedure is performed such as an endoscope, a microscope, a unit having an imaging function such as the imaging unit 515, various kinds of medical procedure instruments, and an examination apparatus. As described above, the robot arm apparatus 510 according to the present embodiment is a medical robot arm apparatus equipped with a medical apparatus. Further, a stereo camera having two imaging units (camera units) may be installed at the front edge of the arm unit 512, and may perform photography so that an imaging target is displayed as a three dimensional (3D) image.

Further, a display device 550 such as a monitor or a display is installed at a position facing the user 520. The captured image of the medical procedure part captured by the imaging unit 515 is displayed on a display screen of the display device 550. The user 520 performs various kinds of treatments while viewing the captured image of the medical procedure part displayed on the display screen of the display device 550.

As described above, in the present embodiment, in the medical field, a technique of performing surgery while photographing the medical procedure part through the robot arm apparatus 510 is proposed. Here, in various kinds of medical procedures including surgery, it is necessary to reduce fatigue or a burden on the user 520 and the patient 540 by performing the medical procedure efficiently. In order to satisfy such a demand, in the robot arm apparatus 510, for example, the following capabilities are considered desirable.

First, as a first point, the robot arm apparatus 510 should secure a task space for surgery. If the arm unit 512 or the imaging unit 515 hinders a field of vision of the practitioner or impedes motion of a hand performing a treatment while the user 520 is performing various kinds of treatments on the medical procedure target 540, the efficiency of surgery is lowered. Further, in FIG. 1, although not illustrated, in an actual surgical scene, for example, a plurality of other doctors and/or nurses performing various support tasks of handing an instrument to the user 520 or checking various kinds of vital signs of the patient 540 are commonly around the user 520 and the patient 540, and there are other devices for performing the support tasks, and thus a surgical environment is complicated. Thus, a small size is desirable in the robot arm apparatus 510.

Next, as a second point, the robot arm apparatus 510 should have high operability for moving the imaging unit 515. For example, the user 520 may desire to observe the same medical procedure part at various positions and angles while performing a treatment on the medical procedure part according to a surgical part or surgical content. In order to change an angle at which the medical procedure part is observed, it is necessary to change an angle of the imaging unit 515 with respect to the medical procedure part, but at this time, it is more desirable that only a photographing angle be changed in a state in which the photographing direction of the imaging unit 515 is fixed to the medical procedure part (that is, while photographing the same part). Thus, for example, the robot arm apparatus 510 should have operability of a high degree of freedom such as a turning movement (a pivot movement) in which the imaging unit 515 moves within a surface of a cone having the medical procedure part as an apex, and an axis of the cone is used as a pivot axis in the state in which the photographing direction of the imaging unit 515 is fixed to the medical procedure part. Since the photographing direction of the imaging unit 515 is fixed to a certain medical procedure part, the pivot movement is also called point lock movement.

Further, in order to change the position and the angle of the imaging unit 515, for example, a method in which the user 520 manually moves the arm unit 512 to move the imaging unit 515 to a desired position and at a desired angle is considered. Thus, it is desirable that there be operability enabling movement of the imaging unit 515, the pivot movement, or the like to be easily performed even with one hand.

Further, there may be a demand from the user 520 to move a photographing center of a captured image captured by the imaging unit 515 from a part on which a treatment is being performed to another part (for example, a part on which a next treatment will be performed) while performing a treatment with both hands during surgery. Thus, various driving methods of the arm unit 512 are necessary such as a method of controlling driving of the arm unit 512 by an operation input from an input unit such as a pedal as well as a method of controlling driving of the arm unit 512 by a manual motion when it is desired to change the position and posture of the imaging unit 515.

As described above as the capability of the second point, the robot arm apparatus 510 should have high operability enabling easy movement, for example, by the pivot movement or the manual motion and satisfying intuition or a desire of the user 520.

Lastly, as a third point, the robot arm apparatus 510 should have stability in the driving control of the arm unit 512. The stability in the driving control of the arm unit 512 may be stability in the position and posture of the front edge unit when the arm unit 512 is driven. The stability in the driving control of the arm unit 512 also includes smooth movement and suppression of vibration (vibration suppression) of the front edge unit when the arm unit 512 is driven. For example, when the front edge unit is the imaging unit 515 as in the example illustrated in FIG. 1, if the position or the posture of the imaging unit 515 is unstable, the captured image displayed on the display screen of the display device 550 is unstable, and the user may have a feeling of discomfort. Particularly, when the robot arm apparatus 510 is used for surgery, a use method in which a stereo camera including two imaging units (camera units) is installed as the front edge unit, and a 3D image generated based on photographed images obtained by the stereo camera is displayed can be assumed. As described above, when the 3D image is displayed, if the position or the posture of the stereo camera is unstable, the user is likely to experience 3D sickness. Further, an observation range photographed by the imaging unit 515 may be enlarged up to about φ15 mm depending on a surgical part or surgical content. When the imaging unit 515 enlarges and photographs a narrow range as described above, slight vibration of the imaging unit 515 is shown as a large shake or deviation of an imaged image. Thus, high positioning accuracy with a permissible range of about 1 mm is necessary for driving control of the arm unit 512 and the imaging unit 515. As described above, high-accuracy responsiveness and high positioning accuracy are necessary in driving control of the arm unit 512.

The inventors have reviewed existing general balance arms and robot arm apparatuses based on position control in terms of the above-mentioned 3 capabilities.

First, with regard to securing the task space for the surgery of the first point, in the general balance arm, a counter balance weight (also called a counter weight or a balancer) for maintaining balance of force when the arm unit is moved is installed inside the base unit or the like, and thus it is difficult to reduce the size of the balance arm apparatus, and it is difficult to say that the corresponding capability is fulfilled.

Further, with regard to the high operability of the second point, in the general balance arm, only some driving of the arm unit, for example, only biaxial driving for moving the imaging unit on a (two-dimensional) plane is electric driving, and manual positioning is necessary for movement of the arm unit and the imaging unit, and thus it is difficult to say that high operability can be implemented. Further, in the general robot arm apparatus based on the position control, since it is difficult to flexibly deal with external force by the position control used for driving control of the arm unit, that is, control of the position and posture of the imaging unit, the position control is commonly called "hard control" and is not suitable of implementing desired operability satisfying the user's intuition.

Further, with regard to stability in driving control of the arm unit of the third point, the joint unit of the arm unit generally has factors that are not easily modelized such as friction, inertia, and the like. In the general balance arm or the robot arm apparatus based on the position control, the factors serve as a disturbance in the driving control of the joint unit, and even when a theoretically appropriate control value (for example, a current value applied to a motor of the joint unit) is given, there are cases in which desired driving (for example, rotation at a desired angle in the motor of the joint unit) is not implemented, and it is difficult to implement high stability necessary for driving control of the arm unit.

As described above, the inventors have reviewed robot arm apparatuses being used for medical purposes and learned that there is a demand for the capabilities of the above-mentioned three points with regard to the robot arm apparatus. However, it is difficult for the general balance arm or the robot arm apparatus based on the position control to easily fulfill such capabilities. The inventors have developed a robot arm apparatus, a robot arm control system, a robot arm control method, and a program according to the present disclosure as a result of reviewing configurations satisfying the capabilities of the three points. Hereinafter, preferred embodiments of the configuration developed by the inventors will be described in detail.

<2. Embodiment of Present Disclosure>

A robot arm control system according to an embodiment of the present disclosure will be described below. In the robot arm control system according to the present embodiment, driving of a plurality of joint units installed in the robot arm apparatus is controlled by whole body cooperative control using generalized inverse dynamics. Further, ideal joint control of implementing an ideal response to a command value by correcting influence of a disturbance is applied to driving control of the joint unit.

In the following description of the present embodiment, an external appearance of the robot arm apparatus according to the present embodiment and a schematic configuration of the robot arm apparatus will be first described in [2-1. External appearance of robot arm apparatus]. Then, an overview of the generalized inverse dynamics and the ideal joint control used for control of the robot arm apparatus according to the present embodiment will be described in [2-2. Generalized inverse dynamics] and [2-3. Ideal joint control]. Then, a configuration of a system for controlling the robot arm apparatus according to the present embodiment will be described with reference to a functional block diagram in [2-4. Configuration of robot arm control system]. Lastly, a specific example of the whole body cooperative control using the generalized inverse dynamics in the robot arm apparatus according to the present embodiment will be described in [2-5. Specific example of purpose of motion].

Further, the following description will proceed with an example in which a front edge unit of an arm unit of a robot arm apparatus according to an embodiment of the present disclosure is an imaging unit, and a medical procedure part is photographed by the imaging unit during surgery as illustrated in FIG. 1 as an embodiment of the present disclosure, but the present embodiment is not limited to this example. The robot arm control system according to the present embodiment can be applied even when a robot arm apparatus including a different front edge unit is used for another purpose.

[2-1. External Appearance of Robot Arm Apparatus]

Figure 2:
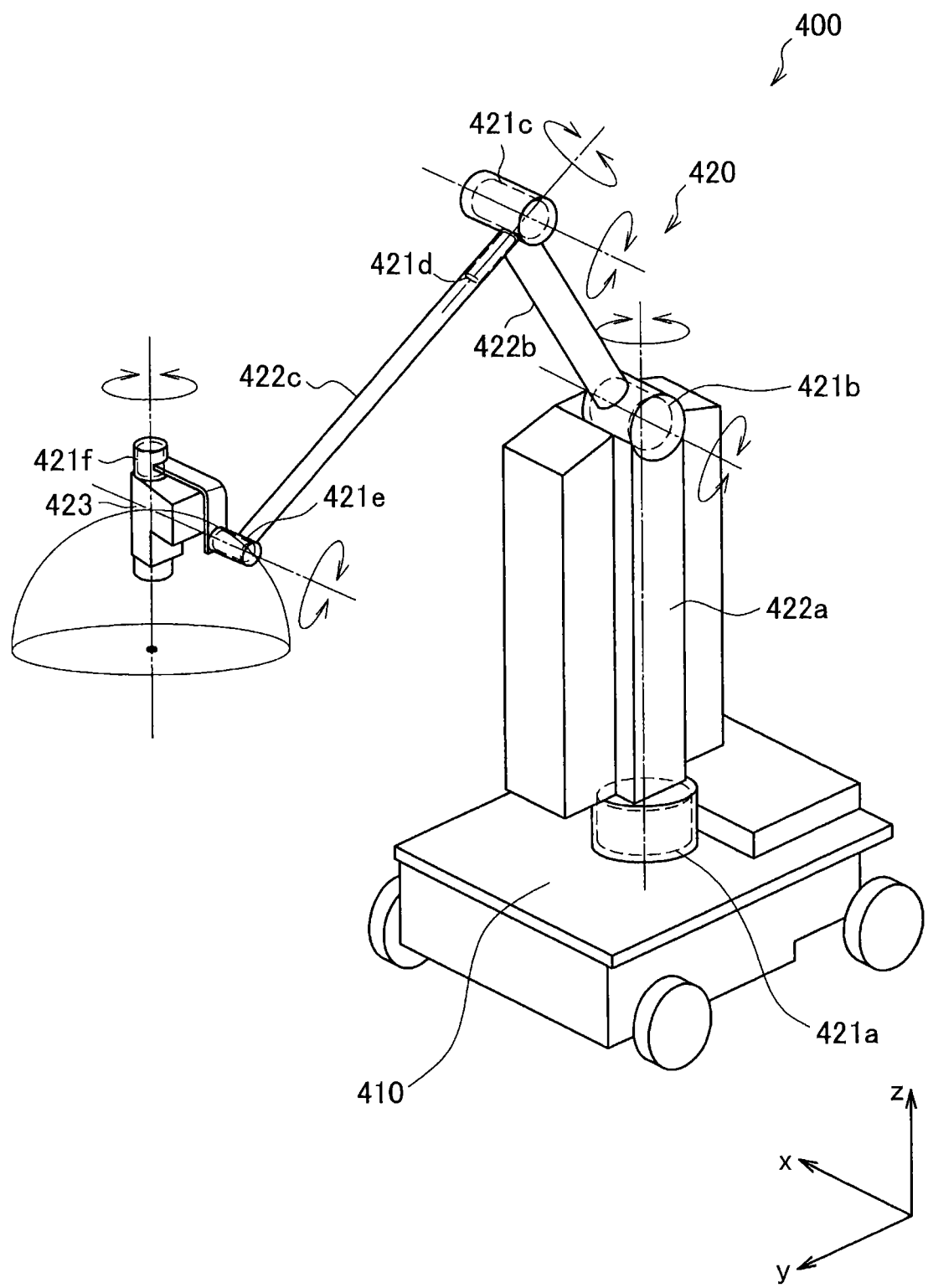
FIG. 2 is a schematic diagram illustrating an external appearance of a robot arm apparatus according to an embodiment of the present disclosure.

First, a schematic configuration of a robot arm apparatus according to an embodiment of the present disclosure will be described with reference to FIG. 2. FIG. 2 is a schematic diagram illustrating an external appearance of a robot arm apparatus according to an embodiment of the present disclosure.

Referring to FIG. 2, a robot arm apparatus 400 according to the present embodiment includes a base unit 410 and an arm unit 420. The base unit 410 serves as the base of the robot arm apparatus 400, and the arm unit 420 extends from the base unit 410. Although not illustrated in FIG. 2, a control unit that controls the robot arm apparatus 400 in an integrated manner may be installed in the base unit 410, and driving of the arm unit 420 may be controlled by the control unit. For example, the control unit is configured with various kinds of signal processing circuits such as a central processing unit (CPU) or a digital signal processor (DSP).

The arm unit 420 includes a plurality of joint units 421a to 421f, a plurality of links 422a to 422c that are connected with one another by the joint units 421a to 421f, and an imaging unit 423 installed at the front edge of the arm unit 420.

The links 422a to 422c are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Further, the imaging unit 423 is connected to the front edge of the arm unit 420, that is, the other end of the link 422c through the joint units 421e and 421f. As described above, the arm shape extending from the base unit 410 is configured such that the base unit 410 serves as a support point, and the ends of the plurality of links 422a to 422c are connected with one another through the joint units 421a to 421f.

The imaging unit 423 is a unit that acquires an image of a photographing target, and is, for example, a camera that captures a moving image, a still image. The driving of the arm unit 420 is controlled such that the position and posture of the imaging unit 423 are controlled. In the present embodiment, for example, the imaging unit 423 photographs some regions of the body of the patient serving as the medical procedure part. Here, the front edge unit installed at the front edge of the arm unit 420 is not limited to the imaging unit 423, and various kinds of medical apparatuses may be connected to the front edge of the arm unit 420 as the front edge unit. As described above, the robot arm apparatus 400 according to the present embodiment is a medical robot arm apparatus equipped with a medical apparatus.

Here, the description of the robot arm apparatus 400 will proceed with coordinate axes defined as illustrated in FIG. 2. Further, a vertical direction, a longitudinal direction, and a horizontal direction are defined according to the coordinate axes. In other words, a vertical direction with respect to the base unit 410 installed on the floor is defined as a z axis direction and a vertical direction. Further, a direction along which the arm unit 420 extends from the base unit 410 as a direction orthogonal to the z axis (that is, a direction in which the imaging unit 423 is positioned with respect to the base unit 410) is defined as a y axis direction and a longitudinal direction. Furthermore, a direction that is orthogonal to the y axis and the z axis is an x axis direction and a horizontal direction.

The joint units 421a to 421f connect the links 422a to 422c to be rotatable. Each of the joint units 421a to 421f includes a rotation mechanism that includes an actuator and is rotationally driven on a certain rotary axis according to driving of the actuator. By controlling rotary driving in each of the joint units 421a to 421f, for example, it is possible to control driving of the arm unit 420 to extend or shorten (fold) the arm unit 420. Here, driving of the joint units 421a to 421f is controlled by the whole body cooperative control which will be described in [2-2. Generalized inverse dynamics] and the ideal joint control which will be described in [2-3. Ideal joint control]. Further, as described above, since the joint units 421a to 421f according to the present embodiment include the rotation mechanism, in the following description, driving control of the joint units 421a to 421f specifically means controlling a rotational angle and/or generated torque (torque generated by the joint units 421a to 421f) of the joint units 421a to 421f.

The robot arm apparatus 400 according to the present embodiment includes the 6 joint units 421a to 421f, and implements 6 degrees of freedom with regard to driving of the arm unit 420. Specifically, as illustrated in FIG. 2, the joint units 421a, 421d, and 421f are installed such that the long axis directions of the links 422a to 422c connected thereto and the photographing direction of the imaging unit 473 connected thereto are set as the rotary axis direction, and the joint units 421b, 421c, and 421e are installed such that an x axis direction serving as a direction in which connection angles of the links 422a to 422c and the imaging unit 473 connected thereto are changed within a y-z plane (a plane specified by the y axis and the z axis) is set as the rotary axis direction. As described above, in the present embodiment, the joint units 421a, 421d, and 421f have a function of performing yawing, and the joint units 421b, 421c, and 421e have a function of performing pitching.

As the above-described configuration of the arm unit 420 is provided, the robot arm apparatus 400 according to the present embodiment can implement the 6 degrees of freedom on driving of the arm unit 420, and thus can freely move the imaging unit 423 within a movable range of the arm unit 420. FIG. 2 illustrates a hemisphere as an exemplary movable range of the imaging unit 423. When the central point of the hemisphere is the photographing center of the medical procedure part photographed by the imaging unit 423, the medical procedure part can be photographed at various angles by moving the imaging unit 423 on the spherical surface of the hemisphere in a state in which the photographing center of the imaging unit 423 is fixed to the central point of the hemisphere.

A configuration of the joint units 421a to 421f illustrated in FIG. 2 will be described herein in further detail with reference to FIG. 3. Further, a configuration of an actuator serving as a component mainly related to the rotary driving of the joint units 421a to 421f among the components of the joint units 421a to 421f will be described herein with reference to FIG. 3.

Figure 3:
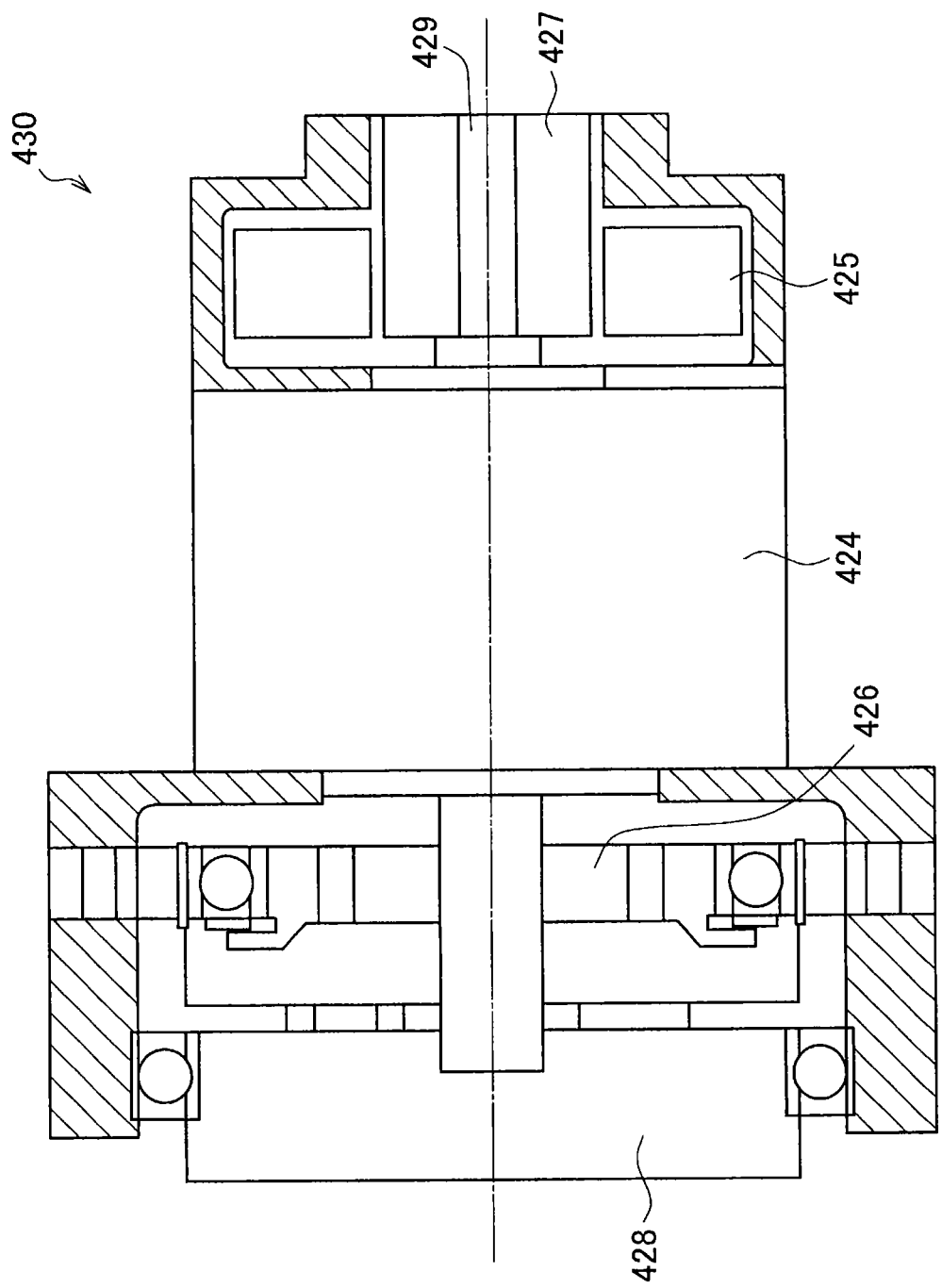
FIG. 3 is a cross-sectional diagram schematically illustrating a state in which an actuator of a joint unit according to an embodiment of the present disclosure is cut along a cross section passing through a rotary axis.

FIG. 3 is a cross-sectional diagram schematically illustrating a state in which an actuator of each of the joint units 421a to 421f according to an embodiment of the present disclosure is cut along a cross section passing through the rotary axis. FIG. 3 illustrates an actuator among the components of the joint units 421a to 421f, but the joint units 421a to 421f may have any other component. For example, the joint units 421a to 421f have various kinds of components necessary for driving of the arm unit 420 such as a control unit for controlling driving of the actuator and a support member for connecting and supporting the links 422a to 422c and the imaging unit 423 in addition to the components illustrated in FIG. 3. Further, in the above description and the following description, driving of the joint unit of the arm unit may mean driving of the actuator in the joint unit.

As described above, in the present embodiment, driving of the joint units 421a to 421f is controlled by the ideal joint control which will be described later in [2-3. Ideal joint control]. Thus, the actuator of the joint units 421a to 421f illustrated in FIG. 3 is configured to perform driving corresponding to the ideal joint control. Specifically, the actuator of the joint units 421a to 421f is configured to be able to adjust the rotational angles and torque associated with the rotary driving in the joint units 421a to 421f. Further, the actuator of the joint units 421a to 421f is configured to be able to arbitrarily adjust a viscous drag coefficient on a rotary motion. For example, it is possible to implement a state in which rotation is easily performed (that is, the arm unit 420 is easily moved by a manual motion) by force applied from the outside or a state in which rotation is not easily performed (that is, the arm unit 420 is not easily moved by a manual motion) by force applied from the outside.

Referring to FIG. 3, an actuator 430 of the joint units 421a to 421f according to the present embodiment includes a motor 424, a motor driver 425, a reduction gear 426, an encoder 427, a torque sensor 428, and a driving shaft 429. As illustrated in FIG. 3, the encoder 427, the motor 424, the reduction gear 426, and the torque sensor 428 are connected to the driving shaft 429 in series in the described order.

The motor 424 is a prime mover in the actuator 430, and causes the driving shaft 429 to rotate about its axis. For example, the motor 424 is an electric motor such as a brushless DC motor. In the present embodiment, as the motor 424 is supplied with an electric current, the rotary driving is controlled.

The motor driver 425 is a driver circuit (a driver integrated circuit (IC)) for supplying an electric current to the motor 424 and rotationally driving the motor 424, and can control the number of revolutions of the motor 424 by adjusting an amount of electric current supplied to the motor 424. Further, the motor driver 425 can adjust the viscous drag coefficient on the rotary motion of the actuator 430 by adjusting an amount of electric current supplied to the motor 424.

The reduction gear 426 is connected to the driving shaft 429, and generates rotary driving force (that is, torque) having a certain value by reducing the rotation speed of the driving shaft 429 generated by the motor 424 at a certain reduction ratio. A high-performance reduction gear of a backlashless type is used as the reduction gear 426. For example, the reduction gear 426 may be a Harmonic Drive (a registered trademark). The torque generated by the reduction gear 426 is transferred to an output member (not illustrated) (for example, a connection member of the links 422a to 422c, the imaging unit 423, or the like) at a subsequent stage through the torque sensor 428 connected to an output shaft of the reduction gear 426.

The encoder 427 is connected to the driving shaft 429, and detects the number of revolutions of the driving shaft 429. It is possible to obtain information such as the rotational angle, the rotational angular velocity, and the rotational angular acceleration of the joint units 421a to 421f based on a relation between the number of revolutions of the driving shaft 429 detected by the encoder and the reduction ratio of the reduction gear 426.

The torque sensor 428 is connected to the output shaft of the reduction gear 426, and detects the torque generated by the reduction gear 426, that is, the torque output by the actuator 430. In the following description, the torque output by the actuator 430 is also referred to simply as "generated torque."

As described above, the actuator 430 can adjust the number of revolutions of the motor 424 by adjusting an amount of electric current supplied to the motor 424. Here, the reduction ratio of the reduction gear 426 may be appropriately set according to the purpose of the robot arm apparatus 400. Thus, the generated torque can be controlled by appropriately adjusting the number of revolutions of the motor 424 according to the reduction ratio of the reduction gear 426. Further, in the actuator 430, it is possible to obtain information such as the rotational angle, the rotational angular velocity, and the rotational angular acceleration of the joint units 421a to 421f based on the number of revolutions of the driving shaft 429 detected by the encoder 427, and it is possible to detect the generated torque in the joint units 421a to 421f through the torque sensor 428.

Further, the torque sensor 428 can detect external torque applied from the outside as well as the generated torque generated by the actuator 430. Thus, as the motor driver 425 adjusts an amount of electric current supplied to the motor 424 based on the external torque detected by the torque sensor 428, it is possible to adjust the viscous drag coefficient on the rotary motion and implement, for example, the state in which rotation is easily or not easily performed by force applied from the outside.

Figure 4A:
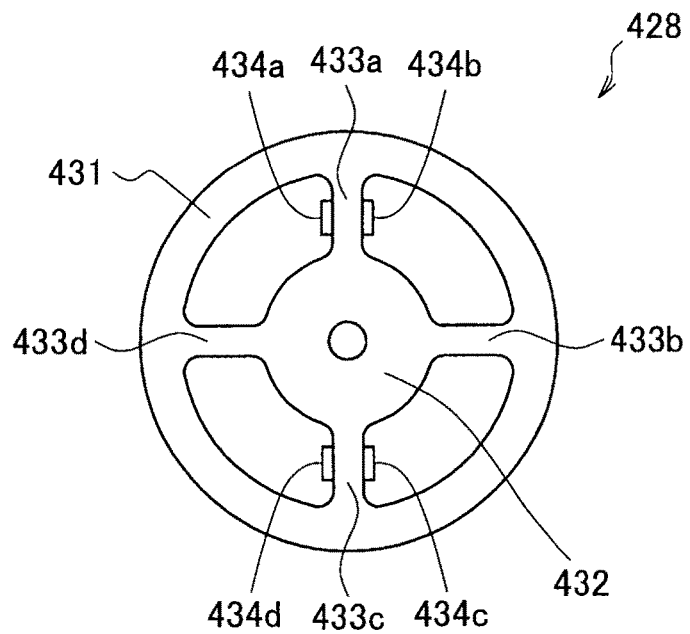
FIG. 4A is a schematic diagram schematically illustrating a state of a torque sensor illustrated in FIG. 3 viewed in an axis direction of a driving shaft.

Here, a configuration of the torque sensor 428 will be described in detail with reference to FIGS. 4A and 4B. FIG. 4A is a schematic diagram schematically illustrating a state of the torque sensor 428 illustrated in FIG. 3 viewed in the axis direction of the driving shaft 429.

Referring to FIG. 4A, the torque sensor 428 includes an outer ring section 431, an inner ring section 432, beam sections 433a to 433d, and distortion detecting elements 434a to 434d. As illustrated in FIG. 4A, the outer ring section 431 and the inner ring section 432 are concentrically arranged. In the present embodiment, the inner ring section 432 is connected to an input side, that is, the output shaft of the reduction gear 426, and the outer ring section 431 is connected to an output side, that is, an output member (not illustrated) at a subsequent stage.

The 4 beam sections 433a to 433d are arranged between the outer ring section 431 and the inner ring section 432 that are concentrically arranged, and connect the outer ring section 431 with the inner ring section 432. As illustrated in FIG. 4A, the beam sections 433a to 433d are interposed between the outer ring section 431 and the inner ring section 432 so that two neighboring sections of the beam sections 433a to 433d form an angle of 90°.

The distortion detecting elements 434a to 434d are installed at the two sections facing each other, that is, disposed at an angle of 180° among the beam sections 433a to 433d. It is possible to detect the generated torque and the external torque of the actuator 430 based on a deformation amount of the beam sections 433a to 433d detected by the distortion detecting elements 434a to 434d.

In the example illustrated in FIG. 4A, among the beam sections 433a to 433d, the distortion detecting elements 434a and 434b are installed at the beam section 433a, and the distortion detecting elements 434c and 434d are installed at the beam section 433c. Further, the distortion detecting elements 434a and 434b are installed with the beam section 433a interposed therebetween, and the distortion detecting elements 434c and 434d are installed with the beam section 433c interposed therebetween. For example, the distortion detecting elements 434a to 434d are distortion gauges attached to the surfaces of the beam sections 433a and 433c, and detect geometric deformation amounts of the beam sections 433a and 433c based on a change in electrical resistance. As illustrated in FIG. 4A, the distortion detecting elements 434a to 434d are installed at 4 positions, and the detecting elements 434a to 434d configure a so-called Wheatstone bridge. Thus, since it is possible to detect distortion using a so-called four-gauge technique, it is possible to reduce influence of interference of shafts other than a shaft in which distortion is detected, eccentricity of the driving shaft 429, a temperature drift, or the like.

As described above, the beam sections 433a to 433d serve as a distortion inducing body whose distortion is detected. The type of the distortion detecting elements 434a to 434d according to the present embodiment is not limited to a distortion gauge, and any other element may be used. For example, the distortion detecting elements 434a to 434d may be elements that detect the deformation amounts of the beam sections 433a to 433d based on a change in magnetic characteristics.

Although not illustrated in FIGS. 3 and 4A, the following configuration may be applied in order to improve the detection accuracy of the generated torque and the external torque by the torque sensor 428. For example, when portions of the beam sections 433a to 433d which are connected with the outer ring section 431 are formed at a thinner thickness than other portions, since a support moment is released, linearity of a deformation amount to be detected is improved, and influence by a radial load is reduced. Further, when both the outer ring section 431 and the inner ring section 432 are supported by a housing through a bearing, it is possible to exclude an action of other axial force and a moment from both the input shaft and the output shaft. Further, in order to reduce another axial moment acting on the outer ring section 431, a support bearing may be arranged at the other end of the actuator 430 illustrated in FIG. 3, that is, a portion at which the encoder 427 is arranged.

The configuration of the torque sensor 428 has been described above with reference to FIG. 4A. As described above, through the configuration of the torque sensor 428 illustrated in FIG. 4A, it is possible to detect the generated torque and the external torque of the actuator 430 with a high degree of accuracy.

Here, in the present embodiment, the configuration of the torque sensor 428 is not limited to the configuration illustrated in FIG. 4A and may be any other configuration. Another exemplary configuration of the torque sensor applied to the actuator 430 other than the torque sensor 428 will be described with reference to FIG. 4B.

Figure 4B:
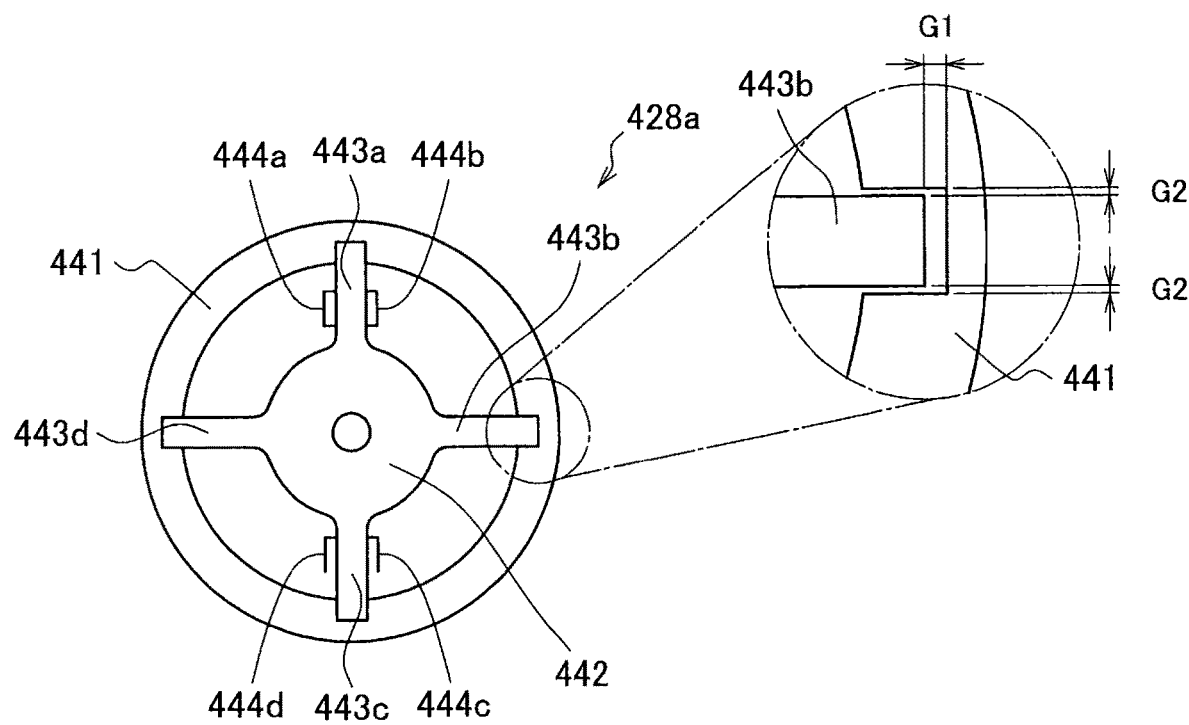
FIG. 4B is a schematic diagram illustrating another exemplary configuration of a torque sensor applied to the actuator illustrated in FIG. 3.

FIG. 4B is a schematic diagram illustrating another exemplary configuration of the torque sensor applied to the actuator 430 illustrated in FIG. 3. Referring to FIG. 4B, a torque sensor 428a according to the present modified example includes an outer ring section 441, an inner ring section 442, beam sections 443a to 443d, and distortion detecting elements 444a to 444d. FIG. 4B schematically illustrates a state of the torque sensor 428a viewed in the axis direction of the driving shaft 429, similarly to FIG. 4A.

In the torque sensor 428a, functions and configurations of the outer ring section 441, the inner ring section 442, the beam sections 443a to 443d, and the distortion detecting elements 444a to 444d are similar to the functions and the configurations of the outer ring section 431, the inner ring section 432, the beam sections 433a to 433d, and the distortion detecting elements 434a to 434d of the torque sensor 428 described above with reference to FIG. 4A. The torque sensor 428a according to the present modified example differs in a configuration of a connection portion of the beam sections 443a to 443d and the outer ring section 441. Thus, the torque sensor 428a illustrated in FIG. 4B will be described focusing on a configuration of the connection portion of the beam sections 443a to 443d and the outer ring section 441 that is the difference with the torque sensor 428 illustrated in FIG. 4A, and a description of a duplicated configuration will be omitted.

Referring to FIG. 4B, the connection portion of the beam section 443b and the outer ring section 441 is enlarged and illustrated together with a general view of the torque sensor 428a. In FIG. 4B, only the connection portion of the beam section 443b and the outer ring section 441 which is one of the four connection portions of the beam sections 443a to 443d and the outer ring section 441 is enlarged and illustrated, but the other 3 connection portions of the beam sections 443a, 443c, and 443d and the outer ring section 441 have the same configuration.

Referring to an enlarged view in FIG. 4B, in the connection portion of the beam section 443b and the outer ring section 441, an engagement concave portion is formed in the outer ring section 441, and the beam section 443b is connected with the outer ring section 441 such that the front edge of the beam section 443b is engaged with the engagement concave portion. Further, gaps G1 and G2 are formed between the beam section 443b and the outer ring section 441. The gap G1 indicates a gap between the beam section 443b and the outer ring section 441 in a direction in which the beam section 443b extends toward the outer ring section 441, and the gap G2 indicates a gap between the beam section 443b and the outer ring section 441 in a direction orthogonal to that direction.

As described above, in the torque sensor 428a, the beam sections 443a to 443d and the outer ring section 441 are arranged to be separated from each other with the certain gaps G1 and G2. In other words, in the torque sensor 428a, the outer ring section 441 is separated from the inner ring section 442. Thus, since the inner ring section 442 has a degree of freedom of a motion without being bound to the outer ring section 441, for example, even when vibration occurs at the time of driving of the actuator 430, a distortion by vibration can be absorbed by the air gaps G1 and G2 between the inner ring section 442 and the outer ring section 441. Thus, as the torque sensor 428a is applied as the torque sensor of the actuator 430, the generated torque and the external torque are detected with a high degree of accuracy.

For example, JP 2009-269102A and JP 2011-209099A which are patent applications previously filed by the present applicant can be referred to for the configuration of the actuator 430 corresponding to the ideal joint control illustrated in FIGS. 3, 4A, and 4B.

The schematic configuration of the robot arm apparatus 400 according to the present embodiment has been described above with reference to FIGS. 2, 3, 4A, and 4B. Next, the whole body cooperative control and the ideal joint control for controlling driving of the arm unit 420, that is, driving of the joint units 421a to 421f in the robot arm apparatus 400 according to the present embodiment, will be described.

[2-2. Generalized Inverse Dynamics]

Next, an overview of the generalized inverse dynamics used for the whole body cooperative control of the robot arm apparatus 400 according to the present embodiment will be described.

The generalized inverse dynamics are basic operations in whole body cooperative control of a multi-link structure of converting purposes of motion related to various dimensions in various kinds of operation spaces into torque to be generated by a plurality of joint units in view of various kinds of constraint conditions in a multi-link structure (for example, the arm unit 420 illustrated in FIG. 2 in the present embodiment) configured such that a plurality of links are connected by a plurality of joint units.

The operation space is an important concept in the force control of the robot apparatus. The operation space is a space for describing a relation between force acting on the multi-link structure and acceleration of the multi-link structure. When the driving control of the multi-link structure is performed by the force control rather than the position control, the concept of the operation space is necessary in the case in which a way of dealing with the multi-link structure and the environment is used as a constraint condition. The operation space is, for example, a space to which the multi-link structure belongs such as a joint space, a Cartesian space, or a momentum space.

The purpose of motion indicates a target value in the driving control of the multi-link structure, and, for example, a target value of a position, a speed, acceleration, force, or an impedance of the multi-link structure that is desired to be achieved through the driving control.

The constraint condition is a constraint condition related to, for example, a position, a speed, acceleration, or force of the multi-link structure that is decided by the shape or the structure of the multi-link structure, the environment around the multi-link structure, a setting performed by the user, or the like. For example, the constraint condition includes information about generated force, a priority, the presence or absence of a non-driven joint, vertical reactive force, a friction weight, a support polygon, and the like.

In the generalized dynamics, in order to achieve both stability of numeric calculation and real-time processable operation efficiency, an operation algorithm is configured with a virtual force decision process (a virtual force calculating process) serving as a first stage and an actual force conversion process (an actual force calculating process) serving as a second stage. In the virtual force calculating process serving as the first stage, virtual force serving as virtual force that is necessary for achieving each purpose of motion and acts on the operation space is decided in view of a priority of a purpose of motion and a maximum value of the virtual force. In the actual force calculating process serving as the second stage, the calculated virtual force is converted into actual force that can be implemented by a configuration of an actual multi-link structure such as joint force or external force in view of a constraint related to a non-driven joint, vertical reactive force, a friction weight, a support polygon, or the like. The virtual force calculating process and the actual force calculating process will be described below. In the following description of the virtual force calculating process, the actual force calculating process, and the ideal joint control, for easier understanding, there are cases in which an exemplary configuration of the arm unit 420 of the robot arm apparatus 400 according to the present embodiment illustrated in FIGS. 2 and 3 is described as a specific example.

(2-2-1. Virtual Force Calculating Process)

A vector configured with certain physical quantities in the joint units of the multi-link structure is referred to as a "generalized variable q" (also referred to as a "joint value q" or a "joint space q"). An operation space x is defined by the following Equation (1) using a time differential value of the generalized variable q and a Jacobian J:

[Math 1]

$$\dot{x} = J\dot{q} \tag{1}$$

In the present embodiment, for example, q indicates a rotational angle in the joint units 421a to 421f of the arm unit 420. An equation of motion related to the operation space x is described by the following Equation (2):

[Math 2]

$$\ddot{x} = \Lambda^{-1} f + c \tag{2}$$

Here, f indicates force acting on the operation space x. Further, $\Lambda^{-1}$ indicates an operation space inertia inverse matrix, c indicates operation space bias acceleration, and $\Lambda^{-1}$ and c are expressed by the following Equations (3) and (4).

[Math 3]

$$\Lambda^{-1} = JH^{-1}J^T \tag{3}$$

$$c = JH^{-1}(\tau - b) + \dot{J}\dot{q} \tag{4}$$

H indicates a joint space inertia matrix, τ indicates joint force (for example, generated torque in the joint units 421a to 421f) corresponding to the joint value q, and b is a term indicating gravity, Coriolis force, or centrifugal force.

In the generalized inverse dynamics, the purpose of motion of the position and the speed related to the operation space x is known to be expressed as acceleration of the operation space x. At this time, in order to implement the operation space acceleration serving as the target value given as the purpose of motion from Equation (1), virtual force $f_v$ that has to act on the operation space x is obtained by solving a sort of linear complementary problem (LCP) expressed by the following Equation (5).

[Math 4]

$$w + \ddot{x} = \Lambda^{-1} f_v + c \qquad (5)$$

$$s.t. \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ are set to a negative lower limit value (including $-\infty$) of an i-th component of $f_v$ and a positive upper limit value (including $+\infty$) of the i-th component of $f_v$. The LCP can be solved, for example, using an iterative technique, a pivot technique, a method using robust acceleration control, or the like.

Further, the operation space inertia inverse matrix $\Lambda^{-1}$ and the bias acceleration c are large in a calculation cost when they are calculated as in Equations (3) and (4) serving as definitional equations. Thus, a method of performing the calculation process of the operation space inertia inverse matrix $\Lambda^{-1}$ at a high speed by applying a quasidynamics calculation (FWD) of calculating generalized acceleration (joint acceleration) from generalized force (the joint force τ) of the multi-link structure has been proposed. Specifically, the operation space inertia inverse matrix $\Lambda^{-1}$ and the bias acceleration c can be obtained based on information related to force acting on the multi-link structure (for example, the arm unit 420 and the joint units 421a to 421f) such as the joint space q, the joint force τ, or the gravity g using the forward dynamics calculation FWD. As described above, the operation space inertia inverse matrix $\Lambda^{-1}$ can be calculated with a calculation amount of O(N) on the number N of joint units by applying the forward dynamics calculation FWD related to the operation space.

Here, as a setting example of the purpose of motion, a condition for achieving the target value (indicated by adding a bar above a second order differential of x) of the operation space acceleration by the virtual force $f_{vi}$ of an absolute value $F_i$ or less can be expressed by the following Equation (6):

[Math 5]

$$L_i = -F_i,$$

$$U_i = F_i,$$

$$\ddot{x}_i = \overline{\ddot{x}}_i \qquad (6)$$

As described above, the purpose of motion related to the position and the speed of the operation space x can be represented as the target value of the operation space acceleration and is specifically expressed by the following Equation (7) (the target value of the position and the speed of the operation space x are indicated by adding a bar above x and a first order differential of x).

[Math 6]

$$\overline{\ddot{x}}_i = K_p(\overline{x}_i - x_i) + K_v(\overline{\dot{x}}_i - \dot{x}_i) \qquad (7)$$

It is also possible to set the purpose of motion related to the operation space (momentum, Cartesian relative coordinates, an interlocked joint, and the like) represented by a linear sum of other operation spaces using an approach of a decomposition operation space. Further, it is necessary to give priorities to competing purposes of motion. The LCP is solved for each priority or in ascending order of priorities, and it is possible to cause virtual force obtained from a previous LCP to act as known external force of a subsequent LCP.

(2-2-2. Actual Force Calculating Process)

In the actual force calculating process serving as the second stage of the generalized inverse dynamics, a process of replacing the virtual force $f_v$ obtained in (2-2-1. Virtual force decision process) with actual joint force and external force is performed. A condition of implementing generalized force $\tau_v = J_v^T f_v$ based on virtual force through generated torque $\tau_a$ generated by the joint unit and external force $f_e$ is expressed by the following Equation (8).

[Math 7]

$$\begin{bmatrix} J_{vu}^T \\ J_{va}^T \end{bmatrix} (f_v - \Delta f_v) = \begin{bmatrix} J_{eu}^T \\ J_{ea}^T \end{bmatrix} f_e + \begin{bmatrix} 0 \\ \tau_a \end{bmatrix} \qquad (8)$$

Here, a subscript a indicates a set of driven joint units (a driven joint set), and a subscript u indicates a set of non-driven joint units (a non-driven joint set). In other words, the upper portions in Equation (8) represent balance of force of a space (a non-driven joint space) by the non-driven joint unit, and the lower portions represent balance of force of a space (a driven joint space) by the driven joint unit. $J_{vu}$ and $J_{va}$ indicate a non-driven joint component and a driven joint component of a Jacobian related to the operation space on which the virtual force $f_v$ acts, respectively. $J_{eu}$ and $J_{ea}$ indicate a non-driven joint component and a driven joint component of a Jacobian related to the operation space on which the external force $f_e$ acts. $\Delta f_v$ indicates a component of the virtual force $f_v$ that is hardly implemented by actual force.

The upper portions in Equation (8) are undefined, and, for example, $f_e$ and $\Delta f_v$ can be obtained by solving a quadratic programming problem (QP) expressed by the following Equation (9).

[Math 8]

$$\min 1/2 \epsilon^T Q_1 \epsilon + 1/2 \xi^T Q_2 \xi$$

$$s.t. U \xi \geq v \qquad (9)$$

Here, $\epsilon$ is a difference between sides of the upper portions in Equation (8), and indicates an equation error. $\xi$ is a connection vector of $f_e$ and $\Delta f_v$, and indicates a variable vector. $Q_1$ and $Q_2$ are positive definite symmetric matrices indicating weights at the time of minimization. Further, an inequality constraint of Equation (9) is used to express a constraint condition related to external force such as vertical reactive force, a friction cone, a maximum value of external force, and a support polygon. For example, an inequality constraint related to a rectangular support polygon is expressed by the following Equation (10).

[Math 9]

$$|F_x| \leq \mu_t F_z,$$

$$|F_y| \leq \mu_t F_z,$$

$$F_z \geq 0,$$

$$|M_x| \leq d_y F_z,$$

$$|M_y| \leq d_x F_z,$$

$$|M_z| \leq \mu_r F_z \qquad (10)$$

Here, z indicates a normal direction of a contact surface, and x and y indicate two orthogonal tangential directions that are vertical to z. $(F_x, F_y, F_z)$ and $(M_x, M_y, M_z)$ are external force and external force moment acting on a contact point. $\mu_t$ and $\mu_r$ indicate friction coefficients related to translation and rotation. $(d_x,d_y)$ indicates a size of a support polygon.

The solutions $f_e$ and $\Delta f_v$ of a minimum norm or a minimum error are obtained from Equations (9) and (10). It is possible to obtain the joint force $\tau_a$ necessary for implementing the purpose of motion by substituting $f_e$ and $\Delta f_v$ obtained from Equation (9) into the lower portion of Equation (8).

In the case of a system in which the basis is fixed, and there is no non-driven joint, all virtual force can be replaced only with joint force, and $f_e=0$ and $\Delta f_v=0$ can be set in Equation (8). In this case, the following Equation (11) can be obtained for the joint force $\tau_a$ from the lower portions in Equation (8).

[Math 10]

$$\tau_a = J_{va}{}^T f_v \qquad (11)$$

The whole body cooperative control using the generalized inverse dynamics according to the present embodiment has been described above. As described above, as the virtual force calculating process and the actual force calculating process are sequentially performed, it is possible to obtain the joint force $\tau_a$ for achieving a desired purpose of motion. In other words, conversely, as the calculated joint force $\tau_a$ is reflected in a theoretical model in motion of the joint units 421a to 421f, the joint units 421a to 421f are driven to achieve a desired purpose of motion.

Further, for example, JP 2009-95959A and JP 2010-188471A which are patent applications previously filed by the present applicant can be referred to for the whole body cooperative control using the generalized inverse dynamics described above, particularly, for the details of a process of deriving the virtual force $f_v$, a method of solving the LCP and obtaining the virtual force $f_v$, the resolution to the QP problem, and the like.

[2-3. Ideal Joint Control]

Next, the ideal joint control according to the present embodiment will be described. Motion of each of the joint units 421a to 421f is modelized by an equation of motion of a second order delay system of the following Equation (12):

[Math 11]

$$I_a \ddot{q} = \tau_a + \tau_e - v_a \dot{q} \qquad (12)$$

Here, $I_a$ indicates an inertia moment (inertia) in a joint unit, $\tau_a$ indicates generated torque of the joint units 421a to 421f, $\tau_e$ indicates external torque acting on each of the joint units 421a to 421f, and $v_a$ indicates a viscous drag coefficient in each of the joint units 421a to 421f. Equation (12) can also be regarded as a theoretical model representing motion of the actuator 430 in the joint units 421a to 421f.

As described above in [2-2. Generalized inverse dynamics], through the calculation using the generalized inverse dynamics, it is possible to calculate $\tau_a$ serving as actual force that each of the joint units 421a to 421f has to use to implement the purpose of motion using the purpose of motion and the constraint condition. Thus, ideally, a response according to the theoretical model expressed by Equation (12) is implemented, that is, a desired purpose of motion is achieved by applying each calculated $\tau_a$ to Equation (12).

However, practically, there are cases in which an error (a modelization error) between motion of the joint units 421a to 421f and the theoretical model expressed by Equation (12) occurs due to influence of various disturbances. The modelization error is classified into an error caused by a mass property such as a weight, a center of gravity, or a tensor of inertia of the multi-link structure and an error caused by friction, inertia, or the like in the joint units 421a to 421f. Of these, the modelization error of the former caused by the mass property can be relatively easily reduced at the time of construction of the theoretical model by applying high-accuracy computer aided design (CAD) data or an identification method.

Meanwhile, the modelization error of the latter caused by friction, inertia, or the like in the joint units 421a to 421f occurs due to a phenomenon that it is difficult to modelize, for example, friction or the like in the reduction gear 426 of the joint units 421a to 421f, and an unignorable modelization error may remain at the time of construction of the theoretical model. Further, there is likely to be an error between a value of an inertia $I_a$ or a viscous drag coefficient $v_a$ in Equation (12) and an actual value in the joint units 421a to 421f. The error that is hardly modelized may act as a disturbance in the driving control of the joint units 421a to 421f. Thus, due to influence of such a disturbance, practically, there are cases in which motion of the joint units 421a to 421f does not respond as in the theoretical model expressed by Equation (12). Thus, there are cases in which it is difficult to achieve the purpose of motion of the control target even when the actual force $\tau_a$ serving as the joint force calculated by the generalized inverse dynamics is applied. In the present embodiment, an active control system is added to each of the joint units 421a to 421f, and thus the response of the joint units 421a to 421f is considered to be corrected such that an ideal response according to the theoretical model expressed by Equation (12) is performed. Specifically, in the present embodiment, torque control of a friction compensation type using the torque sensors 428 and 428a of the joint units 421a to 421f is performed, and in addition, it is possible to perform an ideal response according to an ideal value even on the inertia $I_a$ and the viscous drag coefficient $v_a$ for the requested generated torque $\tau_a$ and the requested external torque $\tau_e$.

In the present embodiment, controlling driving of the joint unit such that the joint units 421a to 421f of the robot arm apparatus 400 perform the ideal response based on the theoretical mode expressed by Equation (12) is referred to as the ideal joint control as described above. Here, in the following description, an actuator whose driving is controlled by the ideal joint control is also referred to as a "virtualized actuator (VA)" since the ideal response is performed. The ideal joint control according to the present embodiment will be described below with reference to FIG. 5.

Figure 5:
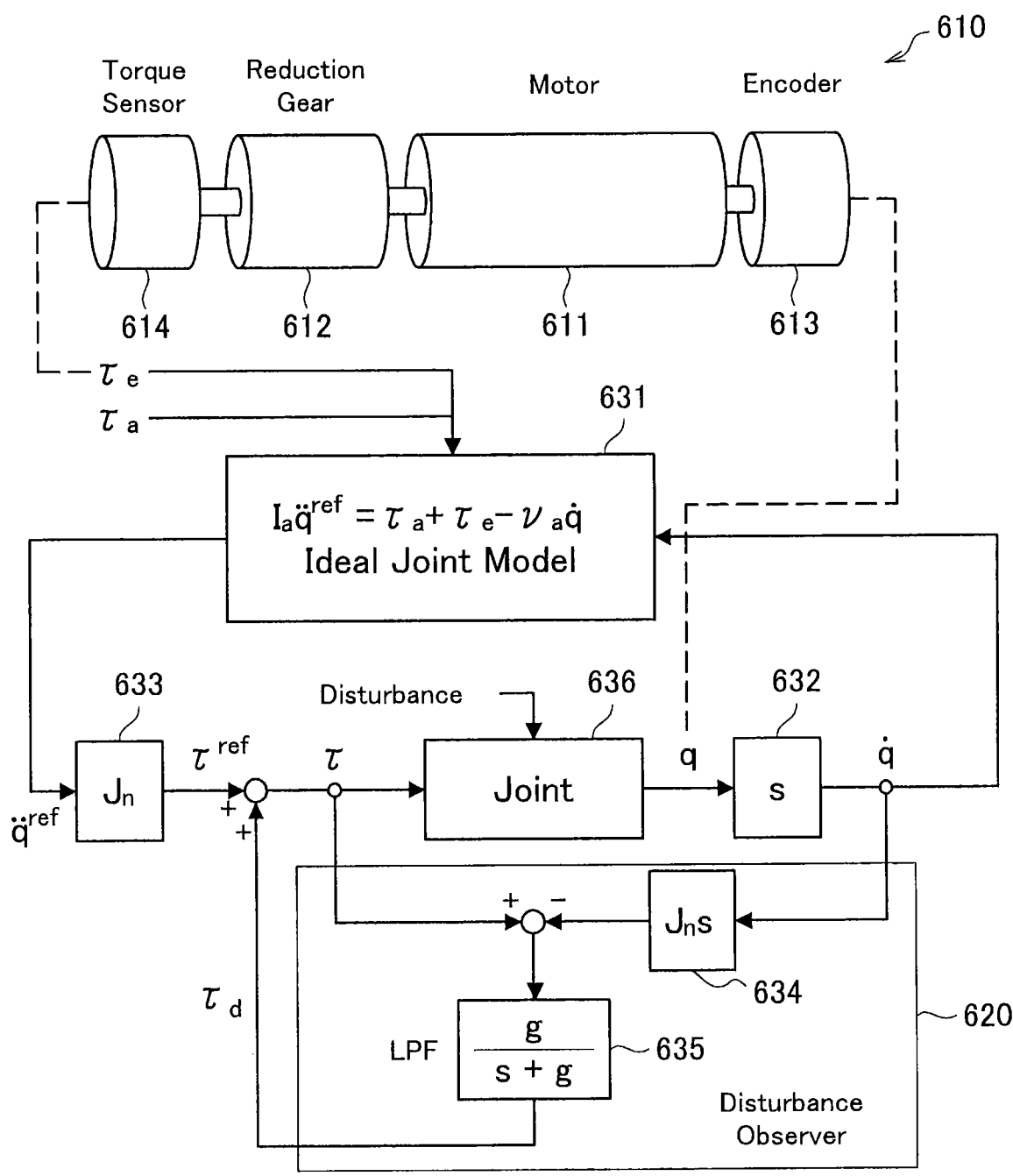
FIG. 5 is an explanatory diagram for describing ideal joint control according to an embodiment of the present disclosure.

FIG. 5 is an explanatory diagram for describing the ideal joint control according to an embodiment of the present disclosure. FIG. 5 schematically illustrates a conceptual computing unit that performs various kinds of operations according to the ideal joint control using blocks.

Referring to FIG. 5, an actuator 610 schematically illustrates a mechanism of the actuator 430 illustrated in FIG. 3, and a motor 611, a reduction gear 612, an encoder 613, and a torque sensor 614 correspond to the motor 424, the reduction gear 426, the encoder 427, and the torque sensor 428 (or the torque sensor 428a illustrated in FIG. 4B) which are illustrated in FIG. 3.

Here, when the actuator 610 performs the response according to the theoretical model expressed by Equation (12), it means that the rotational angular acceleration at the left side is achieved when the right side of Equation (12) is given. Further, as expressed in Equation (12), the theoretical model includes an external torque term $\tau_e$ acting on the actuator 610. In the present embodiment, in order to perform the ideal joint control, the external torque $\tau_e$ is measured by the torque sensor 614. Further, a disturbance observer 620 is applied to calculate a disturbance estimation value $\tau_d$ serving as an estimation value of torque caused by a disturbance based on a rotational angle q of the actuator 610 measured by the encoder 613.

A block 631 represents a computing unit that performs an operation according to the ideal joint model of the joint units 421a to 421f expressed by Equation (12). The block 631 can receive the generated torque $\tau_a$, the external torque $\tau_e$, and the rotational angular velocity (the first order differential of the rotational angle q) and output the rotational angular acceleration target value (a second order differential of a rotational angle target value $q^{ref}$) shown at the left side of Equation (12).

In the present embodiment, the generated torque $\tau_a$ calculated by the method described in [2-2. Generalized inverse dynamics] and the external torque $\tau_e$ measured by the torque sensor 614 are input to the block 631. Meanwhile, the rotational angle q measured by the encoder 613 is input to a block 632 indicating a computing unit that performs differential operation, and thus the rotational angular velocity (the first order differential of the rotational angle q) is calculated. In addition to the generated torque $\tau_a$ and the external torque $\tau_e$, the rotational angular velocity calculated by the block 632 is input to the block 631, and thus the rotational angular acceleration target value is calculated by the block 631. The calculated rotational angular acceleration target value is input to a block 633.

The block 633 indicates a computing unit that calculates torque to be generated in the actuator 610 based on the rotational angular acceleration of the actuator 610. In the present embodiment, specifically, the block 633 can obtain a torque target value $\tau^{ref}$ by multiplying a nominal inertia $J_n$ of the actuator 610 to the rotational angular acceleration target value. In the ideal response, a desired purpose of motion is achieved by causing the actuator 610 to generate the torque target value $\tau^{ref}$, but there are cases in which an actual response is influenced by a disturbance or the like as described above. Thus, in the present embodiment, the disturbance estimation value $\tau_d$ is calculated by the disturbance observer 620, and the torque target value $\tau^{ref}$ is corrected using the disturbance estimation value $\tau_d$.

A configuration of the disturbance observer 620 will be described. As illustrated in FIG. 5, the disturbance observer 620 calculates the disturbance estimation value $\tau_d$ based on a torque command value $\tau$ and the rotational angular velocity calculated from the rotational angle q measured by the encoder 613. Here, the torque command value $\tau$ is a torque value to be finally generated by the actuator 610 after influence of the disturbance is corrected. For example, when no disturbance estimation value $\tau_d$ is calculated, the torque command value $\tau$ is used as the torque target value $\tau^{ref}$.

The disturbance observer 620 is configured with a block 634 and a block 635. The block 634 is a computing unit that calculates torque to be generated by the actuator 610 based on the rotational angular velocity of the actuator 610. In the present embodiment, specifically, the rotational angular velocity calculated by the block 632 based on the rotational angle q measured by the encoder 613 is input to the block 634. The block 634 can obtain the rotational angular acceleration by performing an operation expressed by a transfer function $J_n s$, that is, by differentiating the rotational angular velocity, and calculate an estimation value (a torque estimation value) of torque actually acting on the actuator 610 by multiplying the calculated rotational angular acceleration by the nominal inertia $J_n$.

In the disturbance observer 620, a difference between the torque estimation value and the torque command value $\tau$ is obtained, and thus the disturbance estimation value $\tau_d$ serving as a value of torque by a disturbance is estimated. Specifically, the disturbance estimation value $\tau_d$ may be a difference between the torque command value $\tau$ in the previous control and the torque estimation value in the current control. Since the torque estimation value calculated by the block 634 is based on an actual measurement value, and the torque command value $\tau$ calculated by the block 633 is based on the ideal theoretical model of the joint units 421a to 421f indicated by the block 631, it is possible to estimate influence of a disturbance that is not considered in the theoretical model by obtaining the difference of the two values.

The disturbance observer 620 is further provided with a low pass filter (LPF) indicated by the block 635 in order to prevent a divergence of a system. The block 635 performs an operation represented by a transfer function $g/(s+g)$, outputs only a low frequency component in response to an input value, and stabilizes a system. In the present embodiment, a difference value between the torque estimation value calculated by the block 634 and the torque command value $\tau^{ref}$ is input to the block 635, and the low frequency component is calculated as the disturbance estimation value $\tau_d$.

In the present embodiment, feedforward control of adding the disturbance estimation value $\tau_d$ calculated by the disturbance observer 620 to the torque target value $\tau^{ref}$ is performed, and thus the torque command value $\tau$ serving as a torque value to be finally generated by the actuator 610 is calculated. Then, the actuator 610 is driven based on the torque command value $\tau$. Specifically, the torque command value $\tau$ is converted into a corresponding electric current value (an electric current command value), the electric current command value is applied to the motor 611, so that the actuator 610 is driven.

By employing the configuration described above with reference to FIG. 5, in the driving control of the joint units 421a to 421f according to the present embodiment, even when there is a disturbance component such as friction, it is possible for the response of the actuator 610 to follow the target value. Further, it is possible to perform the ideal response according to the inertia $I_a$ and the viscous drag coefficient $v_a$ assumed by the theoretical model in the driving control of the joint units 421a to 421f.

For example, JP 2009-269102A that is a patent application previously filed by the present applicant can be referred to for the details of the above-described ideal joint control.

The ideal joint control according to the present embodiment has been described above with reference to FIG. 5 together with the generalized inverse dynamics used in the present embodiment. As described above, in the present embodiment, the whole body cooperative control of calculating driving parameters (for example, the generated torque values of the joint units 421a to 421f of the joint units 421a to 421f for achieving the purpose of motion of the arm unit 420 is performed in view of the constraint condition using the generalized inverse dynamics. Further, as described above with reference to FIG. 5, in the present embodiment, as correction in which influence of a disturbance is considered is performed on the generated torque value calculated by the whole body cooperative control using the generalized inverse dynamics, the ideal joint control of implementing the ideal response based on the theoretical model in the driving control of the joint units 421*a* to 421*f* is performed. Thus, in the present embodiment, it is possible to perform high-accuracy driving control for achieving the purpose of motion for driving of the arm unit 420.

[2-4. Configuration of Robot Arm Control System]

Next, a configuration of the robot arm control system according to the present embodiment in which the whole body cooperative control and the ideal joint control described in [2-2. Generalized inverse dynamics] and [2-3. Ideal joint control] are applied to the driving control of the robot arm apparatus will be described.

Figure 6:
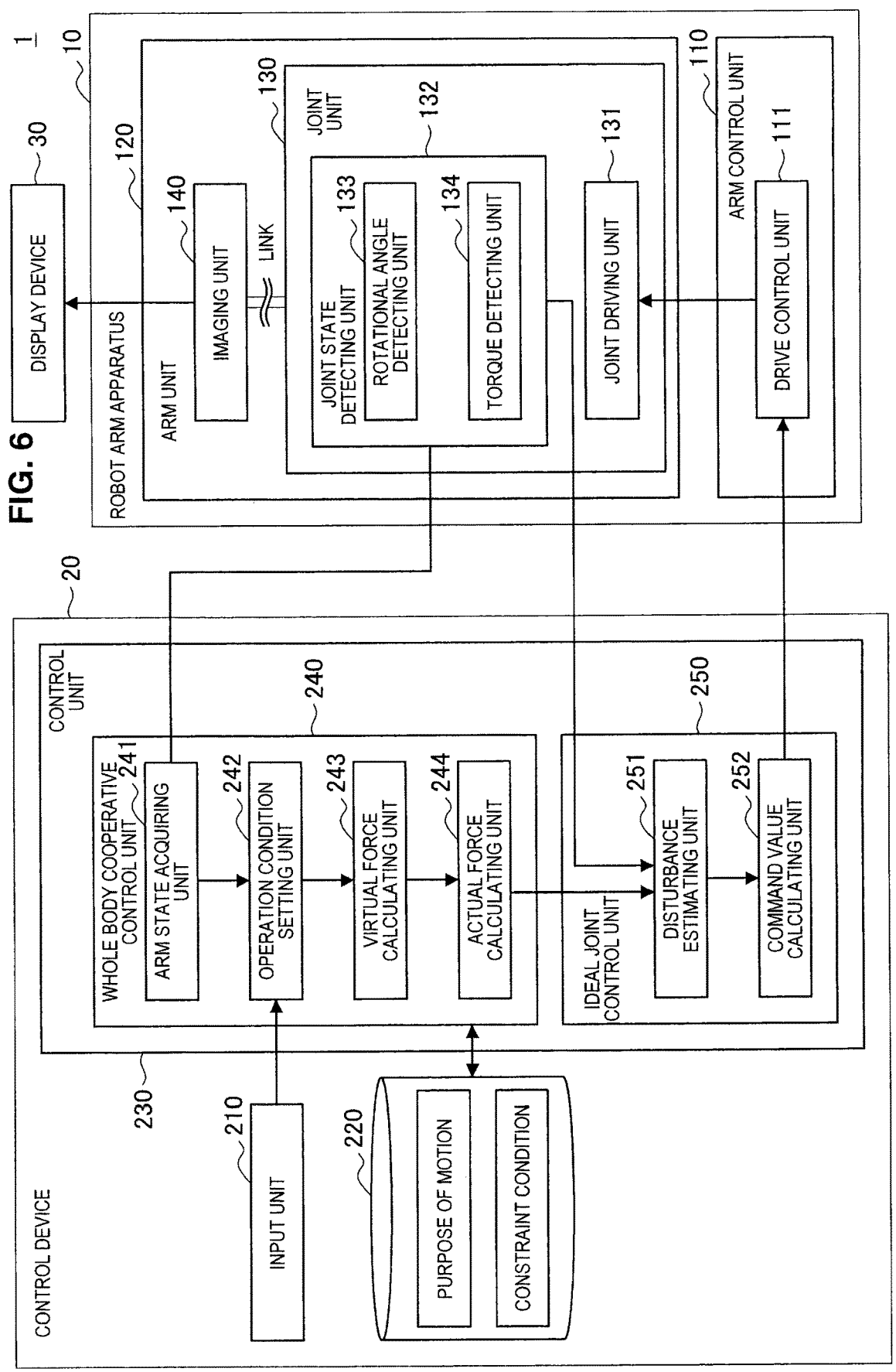
FIG. 6 is a functional block diagram illustrating an exemplary configuration of a robot arm control system according to an embodiment of the present disclosure.

An exemplary configuration of the robot arm control system according to an embodiment of the present disclosure will be described with reference to FIG. 6. FIG. 6 is a functional block diagram illustrating an exemplary configuration of the robot arm control system according to an embodiment of the present disclosure. In the robot arm control system illustrated in FIG. 6, components related to driving control of the arm unit of the robot arm apparatus are mainly illustrated.

Referring to FIG. 6, a robot arm control system 1 according to an embodiment of the present disclosure includes a robot arm apparatus 10, a control device 20, and a display device 30. In the present embodiment, various kinds of operations in the whole body cooperative control described in [2-2. Generalized inverse dynamics] and the ideal joint control described in [2-3. Ideal joint control] through the control device 20 are performed, and driving of the arm unit of the robot arm apparatus 10 is controlled based on the operation result. Further, the arm unit of the robot arm apparatus 10 is provided with an imaging unit 140 which will be described later, and an image captured by the imaging unit 140 is displayed on a display screen of the display device 30. Next, configurations of the robot arm apparatus 10, the control device 20, and the display device 30 will be described in detail.

The robot arm apparatus 10 includes an arm unit having a multi-link structure configured with a plurality of joint units and a plurality of links, and drives the arm unit in the movable range to control the position and posture of the front edge unit installed at the front edge of the arm unit. The robot arm apparatus 10 corresponds to the robot arm apparatus 400 illustrated in FIG. 2.

Referring to FIG. 6, the robot arm apparatus 10 includes an arm control unit 110 and an arm unit 120. The arm unit 120 includes a joint unit 130 and the imaging unit 140.

The arm control unit 110 controls the robot arm apparatus 10 in an integrated manner, and controls driving of the arm unit 120. The arm control unit 110 corresponds to the control unit (not illustrated in FIG. 2) described above with reference to FIG. 2. Specifically, the arm control unit 110 includes a drive control unit 111, and controls driving of the arm unit 120, and driving of the arm unit 120 is controlled by controlling driving of the joint unit 130 according to control of the drive control unit 111. More specifically, the drive control unit 111 controls the number of revolutions of the motor in the actuator of the joint unit 130 and the rotational angle and the generated torque of the joint unit 130 by controlling an amount of electric current supplied to the motor. Here, as described above, driving control of the arm unit 120 by the drive control unit 111 is performed based on the operation result in the control device 20. Thus, an amount of electric current that is controlled by the drive control unit 111 and supplied to the motor in the actuator of the joint unit 130 is an amount of electric current decided based on the operation result in the control device 20.

The arm unit 120 has a multi-link structure configured with a plurality of joint units and a plurality of links, and driving of the arm unit 120 is controlled according to control of the arm control unit 110. The arm unit 120 corresponds to the arm unit 420 illustrated in FIG. 2. The arm unit 120 includes the joint unit 130 and the imaging unit 140. Further, since the plurality of joint units of the arm unit 120 have the same function and configuration, a configuration of one joint unit 130 representing the plurality of joint units is illustrated in FIG. 6.

The joint unit 130 connects links to be rotatable in the arm unit 120, and the rotary driving of the joint unit 130 is controlled according to control of the arm control unit 110 such that the arm unit 120 is driven. The joint unit 130 corresponds to the joint units 421*a* to 421*f* illustrated in FIG. 2. Further, the joint unit 130 includes an actuator, and the actuator has a configuration similar to, for example, the configuration illustrated in FIGS. 3, 4A, and 4B.

The joint unit 130 includes a joint driving unit 131 and a joint state detecting unit 132.

The joint driving unit 131 is a driving mechanism in the actuator of the joint unit 130, and as the joint driving unit 131 is driven, the joint unit 130 is rotationally driven. The drive control unit 111 controls driving of the joint driving unit 131. For example, the joint driving unit 131 is a component corresponding to the motor 424 and the motor driver 425 illustrated in FIG. 3, and driving the joint driving unit 131 corresponds to the motor driver 425 driving the motor 424 with an amount of electric current according to a command given from the drive control unit 111.

The joint state detecting unit 132 detects the state of the joint unit 130. Here, the state of the joint unit 130 may mean a motion state of the joint unit 130. For example, the state of the joint unit 130 includes information such as the rotational angle, the rotational angular velocity, the rotational angular acceleration, and the generated torque of the joint unit 130. In the present embodiment, the joint state detecting unit 132 includes a rotational angle detecting unit 133 that detects the rotational angle of the joint unit 130 and a torque detecting unit 134 that detects the generated torque and the external torque of the joint unit 130. The rotational angle detecting unit 133 and the torque detecting unit 134 correspond to the encoder 427 of the actuator 430 illustrated in FIG. 3 and the torque sensors 428 and 428*a* illustrated in FIGS. 4A and 4B. The joint state detecting unit 132 transmits the detected state of the joint unit 130 to the control device 20.

The imaging unit 140 is an example of the front edge unit installed at the front edge of the arm unit 120, and acquires an image of a photographing target. The imaging unit 140 corresponds to the imaging unit 423 illustrated in FIG. 2. Specifically, the imaging unit 140 is, for example, a camera capable of photographing a photographing target in a moving image format or a still image format. More specifically, the imaging unit 140 includes a plurality of light receiving elements arranged two dimensionally, and can perform photoelectric conversion in the light receiving elements and acquire an image signal indicating an image of a photographing target. The imaging unit 140 transmits the acquired image signal to the display device 30.

Further, similarly to the robot arm apparatus 400 of FIG. 2 in which the imaging unit 423 is installed at the front edge of the arm unit 420, in the robot arm apparatus 10, the imaging unit 140 is actually installed at the front edge of the arm unit 120. In FIG. 6, the form in which the imaging unit 140 is installed at the front edge of the last link through the plurality of joint units 130 and a plurality of links is represented by schematically illustrating the link between the joint unit 130 and the imaging unit 140.

Further, in the present embodiment, various kinds of medical apparatuses may be connected to the front edge of the arm unit 120 as the front edge unit. As the medical apparatus, for example, there are various kinds of units used when the medical procedure is performed such as various kinds of medical procedure instruments including a scalpel or forceps or one unit of various kinds of examination apparatuses including a probe of an ultrasonic examination apparatus. Further, in the present embodiment, the imaging unit 140 illustrated in FIG. 6 or a unit having an imaging function such as an endoscope or a microscope may also be included as a medical apparatus. As described above, the robot arm apparatus 10 according to the present embodiment may be a medical robot arm apparatus including a medical apparatus. Similarly, the robot arm control system 1 according to the present embodiment may be a medical robot arm control system. Further, a stereo camera including two imaging units (camera units) may be installed at the front edge of the arm unit 120, and photography may be performed so that an imaging target is displayed as a 3D image.

The function and configuration of the robot arm apparatus 10 have been described above. Next, a function and configuration of the control device 20 will be described. Referring to FIG. 6, the control device 20 includes an input unit 210, a storage unit 220, and a control unit 230.

The control unit 230 controls the control device 20 in an integrated manner, and performs various kinds of operations for controlling driving of the arm unit 120 in the robot arm apparatus 10. Specifically, in order to control driving of the arm unit 120 of the robot arm apparatus 10, the control unit 230 performs various kinds of operations in the whole body cooperative control and the ideal joint control. The function and configuration of the control unit 230 will be described below in detail, but the whole body cooperative control and the ideal joint control have already been described in [2-2. Generalized inverse dynamics] and [2-3. Ideal joint control], and thus a description thereof will be omitted here.

The control unit 230 includes a whole body cooperative control unit 240 and an ideal joint control unit 250.

The whole body cooperative control unit 240 performs various kinds of operations related to the whole body cooperative control using the generalized inverse dynamics. In the present embodiment, the whole body cooperative control unit 240 acquires a state (an arm state) of the arm unit 120 based on the state of the joint unit 130 detected by the joint state detecting unit 132. Further, the whole body cooperative control unit 240 calculates a control value for the whole body cooperative control of the arm unit 120 in the operation space based on the arm state and the purpose of motion and the constraint condition of the arm unit 120 using the generalized inverse dynamics. For example, the operation space refers to a space for describing a relation between force acting on the arm unit 120 and acceleration generated in the arm unit 120.

The whole body cooperative control unit 240 includes an arm state acquiring unit 241, an operation condition setting unit 242, a virtual force calculating unit 243, and an actual force calculating unit 244.

The arm state acquiring unit 241 acquires the state (the arm state) of the arm unit 120 based on the state of the joint unit 130 detected by the joint state detecting unit 132. Here, the arm state may mean the motion state of the arm unit 120. For example, the arm state includes information such as a position, a speed, acceleration, or force of the arm unit 120. As described above, the joint state detecting unit 132 acquires information such as the rotational angle, the rotational angular velocity, the rotational angular acceleration, or the generated torque of each of the joint units 130 as the state of the joint unit 130. Further, as will be described later, the storage unit 220 stores various kinds of information that is processed by the control device 20, and in the present embodiment, the storage unit 220 may store various kinds of information (arm information) related to the arm unit 120, for example, the number of joint units 130 and the number of links configuring the arm unit 120, a connection state of the link and the joint unit 130, and the length of the link. The arm state acquiring unit 241 can acquire the corresponding information from the storage unit 220. Thus, the arm state acquiring unit 241 can acquire information such as the positions (coordinates) of the plurality of joint units 130, a plurality of links, and the imaging unit 140 on the space (that is, the shape of the arm unit 120 or the position and posture of the imaging unit 140) or force acting on each of the joint units 130, the link, and the imaging unit 140 based on the state of the joint unit 130 and the arm information. The arm state acquiring unit 241 transmits the acquired arm information to the operation condition setting unit 242.

The operation condition setting unit 242 sets an operation condition in an operation related to the whole body cooperative control using the generalized inverse dynamics. Here, the operation condition may be the purpose of motion and the constraint condition. The purpose of motion may be various kinds of information related to a motion of the arm unit 120. Specifically, the purpose of motion may be a target value of the position and posture (coordinates), a speed, acceleration, and force of the imaging unit 140 or a target value of the position (coordinates), a speed, acceleration, and force of the plurality of joint units 130 and a plurality of links of the arm unit 120. The constraint condition may be various kinds of information for constricting the motion of the arm unit 120. Specifically, the constraint condition may be coordinates of a region into which none of the components of the arm unit should move, values of a speed and acceleration at which the arm unit should not move, a value of force that should not be generated, or the like. Further, a constraint range of various kinds of physical quantities in the constraint condition may be set from ones that are difficult for the arm unit 120 to implement structurally or may be appropriately set by the user. Further, the operation condition setting unit 242 includes a physical model (for example, one in which the number of links configuring the arm unit 120, the length of the link, the connection state of the link through the joint unit 130, the movable range of the joint unit 130, and the like are modelized; this corresponds to an internal model) for the structure of the arm unit 120, and may set the motion condition and the constraint condition by generating a control model in which a desired motion condition and a desired constraint condition are reflected in the physical model.

In the present embodiment, it is possible to appropriately set the purpose of motion and the constraint condition and cause the arm unit 120 to perform a desired movement. For example, it is possible to set the target value of the position of the imaging unit 140 as the purpose of motion and move the imaging unit 140 to the target position, and it is also possible to set a movement constraint according to the constraint condition, for example, to prevent the arm unit 120 from invading a certain region in a space and then drive the arm unit 120.

As a specific example of the purpose of motion, for example, the purpose of motion may be a pivot movement serving as a turning movement in which the imaging unit 140 moves within a plane of a cone having a medical procedure part as an apex, and an axis of the cone is used as a pivot axis in a state in which the photographing direction of the imaging unit 140 is fixed to the medical procedure part. In the pivot movement, the turning movement may be performed in a state in which a distance between the imaging unit 140 and a point corresponding to the apex of the cone is maintained constant. As the pivot movement is performed, it is possible to observe an observation part at an equal distance and at different angles, and thus it is possible to improve a convenience of the user performing surgery.

Another specific example, the purpose of motion may be content controlling the generated torque in each of the joint units 130. Specifically, the purpose of motion may be a power assist movement of controlling the state of the joint unit 130 such that gravity acting on the arm unit 120 is negated and controlling the state of the joint unit 130 such that movement of the arm unit 120 is supported in a direction of force given from the outside. More specifically, in the power assist movement, driving of each of the joint units 130 is controlled such that each of the joint units 130 generates the generated torque for negating external torque by gravity in each of the joint units 130 of the arm unit 120, and thus the position and posture of the arm unit 120 are held in a certain state. When external torque is further applied from the outside (for example, from the user) in this state, driving of each of the joint units 130 is controlled such that each of the joint units 1 generates the generated torque in the same direction as the applied external torque. As the power assist movement is performed, when the user manually moves the arm unit 120, the user can move the arm unit 120 by small force, and thus a feeling of moving the arm unit 120 in a non-gravity state can be given to the user. Further, it is possible to combine the pivot movement with the power assist movement.

Here, in the present embodiment, the purpose of motion may mean a movement (motion) of the arm unit 120 implemented in the whole body cooperative control or may mean an instantaneous purpose of motion (that is, the target value in the purpose of motion) in the corresponding movement. For example, in the case of the pivot movement, performing the pivot movement by the imaging unit 140 is the purpose of motion, but, for example, a value of the position or the speed of the imaging unit 140 in the cone plane in the pivot movement is set as an instantaneous purpose of motion (the target value in the purpose of motion) while the pivot movement is being performed. Further, for example, in the case of the power assist movement, performing the power assist movement for supporting movement of the arm unit 120 in the direction of force applied from the outside is the purpose of motion, but a value of the generated torque in the same direction as the external torque applied to each of the joint units 130 is set as an instantaneous purpose of motion (the target value in the purpose of motion) while the power assist movement is being performed. In the present embodiment, the purpose of motion is a concept including both the instantaneous purpose of motion (for example, the target value of the position, the speed, or force of each component of the arm unit 120 during a certain period of time) and movement of each component of the arm unit 120 implemented over time as a result of continuously achieving the instantaneous purpose of motion. In each step in an operation for the whole body cooperative control in the whole body cooperative control unit 240, the instantaneous purpose of motion is set each time, and the operation is repeatedly performed, so that a desired purpose of motion is finally achieved.

Further, in the present embodiment, when the purpose of motion is set, the viscous drag coefficient in the rotary motion of each of the joint units 130 may be appropriately set as well. As described above, the joint unit 130 according to the present embodiment is configured to be able to appropriately adjust the viscous drag coefficient in the rotary motion of the actuator 430. Thus, as the viscous drag coefficient in the rotary motion of each of the joint units 130 is also set at the time of setting of the purpose of motion, for example, it is possible to implement the state in which rotation is easily or not easily performed by force applied from the outside. For example, in the case of the power assist movement, as the viscous drag coefficient in the joint unit 130 is set to be small, the user can move the arm unit 120 by small force, and the user can have a non-gravity feeling. As described above, the viscous drag coefficient in the rotary motion of each of the joint units 130 may be appropriately set according to content of the purpose of motion.

The specific examples of the purpose of motion will be described again in detail in [2-5. Specific example of purpose of motion].

Here, in the present embodiment, as will be described later, the storage unit 220 may store a parameter related to the operation condition such as the purpose of motion or the constraint condition used in an operation related to the whole body cooperative control. The operation condition setting unit 242 can set the constraint condition stored in the storage unit 220 as the constraint condition used in the operation of the whole body cooperative control.

Further, in the present embodiment, the operation condition setting unit 242 can set the purpose of motion by a plurality of methods. For example, the operation condition setting unit 242 may set the purpose of motion based on the arm state transmitted from the arm state acquiring unit 241. As described above, the arm state includes information of the position of the arm unit 120 and information of force acting on the arm unit 120. Thus, for example, when the user manually moves the arm unit 120, information related to how the user moves the arm unit 120 is also acquired as the arm state through the arm state acquiring unit 241. Thus, the operation condition setting unit 242 can set, for example, the position to which the user has moved the arm unit 120, a speed at which the user has moved the arm unit 120, or force by which the user has moved the arm unit 120 as the instantaneous purpose of motion based on the acquired arm state. As the purpose of motion is set as described above, control is performed such that driving of the arm unit 120 follows and supports movement of the arm unit 120 by the user.

Further, for example, the operation condition setting unit 242 may set the purpose of motion based on an instruction input from the input unit 210 by the user. As will be described later, the input unit 210 is an input interface through which the user inputs, for example, information or a command related to driving control of the robot arm apparatus 10 to the control device 20, and in the present embodiment, the purpose of motion may be set based on an operation input from the input unit 210 by the user. Specifically, the input unit 210 includes an operation unit operated by the user such as a lever or a pedal, and, for example, the operation condition setting unit 242 may set the position or the speed of each component of the arm unit 120 as the instantaneous purpose of motion according to an operation of the lever, the pedal, or the like.

Further, for example, the operation condition setting unit 242 may set the purpose of motion stored in the storage unit 220 as the purpose of motion used in the operation of the whole body cooperative control. For example, in the case of the purpose of motion for causing the imaging unit 140 to stop at a certain point in the space, coordinates of the certain point can be set as the purpose of motion in advance. Further, for example, in the case of the purpose of motion for causing the imaging unit 140 to move along a certain trajectory in the space, coordinates of points indicating the certain trajectory can be set as the purpose of motion in advance. As described above, when the purpose of motion can be set in advance, the purpose of motion may be stored in the storage unit 220 in advance. Further, for example, in the case of the pivot movement, the purpose of motion is limited to setting a position, a speed, or the like in the plane of the cone as the target value, and in the case of the power assist movement, the purpose of motion is limited to setting force as the target value. As described above, when the purpose of motion such as the pivot movement or the power assist movement is set in advance, for example, information related to a range or a type of the target value that can be set as the instantaneous purpose of motion in the purpose of motion may be stored in the storage unit 220. The operation condition setting unit 242 can include and set various kinds of information related to the purpose of motion as the purpose of motion.

Further, the user may appropriately set the method of setting the purpose of motion through the operation condition setting unit 242, for example, according to the purpose of the robot arm apparatus 10. Further, the operation condition setting unit 242 may set the purpose of motion and the constraint condition by appropriately combining the above methods. Furthermore, a priority of the purpose of motion may be set to the constraint condition stored in the storage unit 220, and when there are a plurality of different purposes of motion, the operation condition setting unit 242 may set the purpose of motion according to the priority of the constraint condition. The operation condition setting unit 242 transmits the arm state, the set purpose of motion and the constraint condition to the virtual force calculating unit 243.

The virtual force calculating unit 243 calculates virtual force in the operation related to the whole body cooperative control using the generalized inverse dynamics. For example, a virtual force calculation process performed by the virtual force calculating unit 243 may be a series of processes described above in (2-2-1. Virtual force calculating process). The virtual force calculating unit 243 transmits the calculated virtual force $f_v$ to the actual force calculating unit 244.

The actual force calculating unit 244 calculates actual force in the operation related to the whole body cooperative control using the generalized inverse dynamics For example, an actual force calculation process performed by the actual force calculating unit 244 may be a series of processes described above in (2-2-2. Actual force calculating process). The actual force calculating unit 244 transmits the calculated actual force (the generated torque) $\tau_a$ to the ideal joint control unit 250. Further, in the present embodiment, the generated torque $\tau_a$ calculated by the actual force calculating unit 244 is also referred to as a "control value" or a "control torque value" to mean a control value of the joint unit 130 in the whole body cooperative control.

The ideal joint control unit 250 performs various kinds of operations related to the ideal joint control for implementing the ideal response based on the theoretical model. In the present embodiment, the ideal joint control unit 250 corrects influence of a disturbance on the generated torque $\tau_a$ calculated by the actual force calculating unit 244, and calculates the torque command value $\tau$ for implementing the ideal response of the arm unit 120. The operation process performed by the ideal joint control unit 250 corresponds to a series of processes described above in [2-3. Ideal joint control].

The ideal joint control unit 250 includes a disturbance estimating unit 251 and a command value calculating unit 252.

The disturbance estimating unit 251 calculates the disturbance estimation value $\tau_d$ based on the torque command value $\tau$ and the rotational angular velocity calculated from the rotational angle q detected by the rotational angle detecting unit 133. Here, the torque command value $\tau$ refers to the command value indicating the generated torque of the arm unit 120 that is finally transmitted to the robot arm apparatus 10. As described above, the disturbance estimating unit 251 has a function corresponding to the disturbance observer 620 illustrated in FIG. 5.

The command value calculating unit 252 calculates the torque command value $\tau$ serving as the command value indicating torque that is generated by the arm unit 120 and finally transmitted to the robot arm apparatus 10 using the disturbance estimation value $\tau_d$ calculated by the disturbance estimating unit 251. Specifically, the command value calculating unit 252 calculates the torque command value $\tau$ by adding the disturbance estimation value $\tau_d$ calculated by the disturbance estimating unit 251 to $\tau^{ref}$ calculated from the ideal model of the joint unit 130 expressed by Equation (12). For example, when the disturbance estimation value $\tau_d$ is not calculated, the torque command value $\tau$ is used as the torque target value $\tau^{ref}$. As described above, the function of the command value calculating unit 252 corresponds to a function other than that of the disturbance observer 620 illustrated in FIG. 5.

As described above, in the ideal joint control unit 250, a series of processes described above with reference to FIG. 5 is performed such that information is repeatedly exchanged between the disturbance estimating unit 251 and the command value calculating unit 252. The ideal joint control unit 250 transmits the calculated torque command value $\tau$ to the drive control unit 111 of the robot arm apparatus 10. The drive control unit 111 performs control of supplying an amount of electric current corresponding to the transmitted torque command value $\tau$ to the motor in the actuator of the joint unit 130, controls the number of revolutions of the motor, and controls the rotational angle and the generated torque of the joint unit 130.

In the robot arm control system 1 according to the present embodiment, since driving control of the arm unit 120 in the robot arm apparatus 10 is continuously performed while a task using the arm unit 120 is being performed, the above-described process is repeatedly performed in the robot arm apparatus 10 and the control device 20. In other words, the joint state detecting unit 132 of the robot arm apparatus 10 detects the state of the joint unit 130, and transmits the detected state of the joint unit 130 to the control device 20. In the control device 20, various kinds of operations related to the whole body cooperative control and the ideal joint control for controlling driving of the arm unit 120 are performed based on the state of the joint unit 130, the purpose of motion, and the constraint condition, and the torque command value $\tau$ serving as the operation result is transmitted to the robot arm apparatus 10. In the robot arm apparatus 10, driving of the arm unit 120 is controlled based on the torque command value $\tau$, and the state of the joint unit 130 during or after driving is detected by the joint state detecting unit 132 again.

The description of the other components of the control device 20 will now continue.

The input unit 210 is an input interface through which the user inputs, for example, information or a command related to driving control of the robot arm apparatus 10 to the control device 20. In the present embodiment, based on an operation input from the input unit 210 by the user, driving of the arm unit 120 of the robot arm apparatus 10 may be controlled, and the position and posture of the imaging unit 140 may be controlled. Specifically, as described above, as the user inputs instruction information related to an instruction of arm driving input from the input unit 210 to the operation condition setting unit 242, the operation condition setting unit 242 may set the purpose of motion in the whole body cooperative control based on the instruction information. As described above, the whole body cooperative control is performed using the purpose of motion based on the instruction information input by the user, and thus driving of the arm unit 120 according to the user's operation input is implemented.

Specifically, the input unit 210 includes an operation unit operated by the user such as a mouse, a keyboard, a touch panel, a button, a switch, a lever, and a pedal, for example. For example, when the input unit 210 includes a pedal, the user can control driving of the arm unit 120 by operating the pedal by foot. Thus, even when the user performs a treatment on the patient's medical procedure part using both hands, it is possible to adjust the position and posture of the imaging unit 140, that is, the photographing position or the photographing angle of the medical procedure part through an operation of the pedal by foot.

The storage unit 220 stores various kinds of pieces of information that are processed by the control device 20. In the present embodiment, the storage unit 220 can store various kinds of parameters used in the operation related to the whole body cooperative control and the ideal joint control performed by the control unit 230. For example, the storage unit 220 may store the purpose of motion and the constraint condition used in the operation related to the whole body cooperative control performed by the whole body cooperative control unit 240. The purpose of motion stored in the storage unit 220 may be a purpose of motion that can be set in advance so that the imaging unit 140 can stop at a certain point in the space as described above, for example. Further, the constraint condition may be set by the user in advance according to the geometric configuration of the arm unit 120, the purpose of the robot arm apparatus 10, or the like and then stored in the storage unit 220. Furthermore, the storage unit 220 may store various kinds of information related to the arm unit 120 used when the arm state acquiring unit 241 acquires the arm state. Moreover, the storage unit 220 may store, for example, the operation result in the operation related to the whole body cooperative control and the ideal joint control performed by the control unit 230 and numerical values calculated in the operation process. As described above, the storage unit 220 may store all parameters related to various kinds of processes performed by the control unit 230, and the control unit 230 can perform various kinds of processes while transmitting or receiving information to or from the storage unit 220.

The function and configuration of the control device 20 have been described above. The control device 20 according to the present embodiment may be configured, for example, with various kinds of information processing devices (arithmetic processing devices) such as a personal computer (PC) or a server. Next, a function and configuration of the display device 30 will be described.

The display device 30 displays various kinds of information on the display screen in various formats such as text or an image, and visually notifies the user of the information. In the present embodiment, the display device 30 displays an image captured by the imaging unit 140 of the robot arm apparatus 10 through the display screen. Specifically, the display device 30 includes a function or component such as an image signal processing unit (not illustrated) that performs various kinds of image processing on the image signal acquired by the imaging unit 140 or a display control unit (not illustrated) that performs control such that an image based on the processed image signal is displayed on the display screen. Further, the display device 30 may have various kinds of functions and components that are equipped in a general display device in addition to the above function or component. The display device 30 corresponds to the display device 550 illustrated in FIG. 1.

The functions and configurations of the robot arm apparatus 10, the control device 20, and the display device 30 according to the present embodiment have been described above with reference to FIG. 6. Each of the above components may be configured using a versatile member or circuit, and may be configured by hardware specialized for the function of each component. Further, all the functions of the components may be performed by a CPU or the like. Thus, a configuration to be used may be appropriately changed according to a technology level when the present embodiment is carried out.

As described above, according to the present embodiment, the arm unit 120 having the multi-link structure in the robot arm apparatus 10 has at least 6 or more degrees of freedom, and driving of each of the plurality of joint units 130 configuring the arm unit 120 is controlled by the drive control unit 111. Further, the medical apparatus is installed at the front edge of the arm unit 120. As driving of each joint unit 130 is controlled as described above, driving control of the arm unit 120 having a high degree of freedom is implemented, and the robot arm apparatus 10 for medical use having high operability for a user is implemented.

More specifically, according to the present embodiment, in the robot arm apparatus 10, the state of the joint unit 130 is detected by the joint state detecting unit 132. Further, in the control device 20, based on the state of the joint unit 130, the purpose of motion, and the constraint condition, various kinds of operations related to the whole body cooperative control using the generalized inverse dynamics for controlling driving of the arm unit 120 are performed, and torque command value $\tau$ serving as the operation result are calculated. Furthermore, in the robot arm apparatus 10, driving of the arm unit 120 is controlled based on the torque command value $\tau$. As described above, in the present embodiment, driving of the arm unit 120 is controlled by the whole body cooperative control using the generalized inverse dynamics. Thus, driving control of the arm unit 120 according to the force control is implemented, and the robot arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving units for moving the arm unit 120 manually or through an operation input from a pedal are implemented, and thus user convenience is further improved.

Further, in the present embodiment, the whole body cooperative control and the ideal joint control are applied to driving control of the arm unit 120. In the ideal joint control, a disturbance component such as friction or inertia in the joint unit 130 is estimated, and feedforward control is performed using the estimated disturbance component. Thus, even when there is a disturbance component such as friction, the ideal response can be implemented on driving of the joint unit 130. Thus, small influence of vibration or the like, high-accuracy responsiveness, and high positioning accuracy or stability are implemented in driving control of the arm unit 120.

Further, in the present embodiment, each of the plurality of joint units 130 configuring the arm unit 120 has a configuration suitable for the ideal joint control illustrated in FIG. 3, for example, and the rotational angle, the generated torque and the viscous drag coefficient of each of the joint units 130 can be controlled according to an electric current value. As described above, driving of each of the joint units 130 is controlled according to an electric current value, and driving of each of the joint units 130 is controlled according to the whole body cooperative control while detecting the entire state of the arm unit 120, and thus the counter balance is unnecessary, and the small robot arm apparatus 10 is implemented.

[2-5. Specific Example of Purpose of Motion]

Next, a specific example of the purpose of motion according to the present embodiment will be described. As described above in [2-4. Configuration of the robot arm control system], in the present embodiment, various kinds of purposes of motion are implemented by the whole body cooperative control. Here, as a specific example of the purpose of motion according to the present embodiment, the power assist movement and the pivot movement will be described. In the following description of the specific example of the purpose of motion, components of the robot arm control system according to the present embodiment are indicated using reference numerals in the functional block diagram illustrated in FIG. 6.

The power assist movement is a movement of controlling the state of the joint unit 130 such that gravity acting on the arm unit 120 is negated and controlling the state of the joint unit 130 such that movement of the arm unit 120 in a direction of force applied from the outside is supported. Specifically, when the user manually moves the arm unit 120, the power assist movement is a movement of controlling driving of the arm unit 120 such that force applied by the user is supported. More specifically, in order to implement the power assist movement, first, external torque is detected by the torque detecting unit 134 in a state in which no force other than gravity acts on the arm unit 120, and the instantaneous purpose of motion is set so that the generated torque for negating the detected external torque is generated by each of the joint units 130. At this stage, the position and posture of the arm unit 120 are held in a certain state. When external torque is further applied from the outside (for example, from the user) in this state, additionally applied external torque is detected by the torque detecting unit 134, and the instantaneous purpose of motion is further set such that each of the joint units 130 generates generated torque in the same direction as the detected additional external torque. As driving of each of the joint units 130 is controlled according to the instantaneous purpose of motion, the power assist movement is implemented. Through the power assist movement, the user can move the arm unit by small force, and thus the user can have a feeling of moving the arm unit 120 in a non-gravity state, and the operability of the arm unit 120 by the user is improved.

The pivot movement is a turning movement in which the front edge unit installed at the front edge of the arm unit 120 moves on a plane of a cone having a certain point in the space as an apex in a state in which a direction of the front edge unit is fixed on the certain point, and an axis of the cone is used as a pivot axis. Specifically, when the front edge unit is the imaging unit 140, the pivot movement is a turning movement in which the imaging unit 140 installed at the front edge of the arm unit 120 moves on a plane of a cone having a certain point in a space as an apex in a state in which the photographing direction of the imaging unit 140 is fixed on the certain point, and an axis of the cone is used as a pivot axis. As a point corresponding to the apex of the cone in the pivot movement, for example, the medical procedure part is selected. Further, in the pivot movement, the turning movement may be performed in a state in which a distance between the front edge unit or the imaging unit 140 and the point corresponding to the apex of the cone is maintained constant. Further, since the direction of the front edge unit or the photographing direction of the imaging unit 140 is fixed on a certain point (for example, the medical procedure part) in the space, the pivot movement is also referred to as a "point lock movement."

Figure 7:
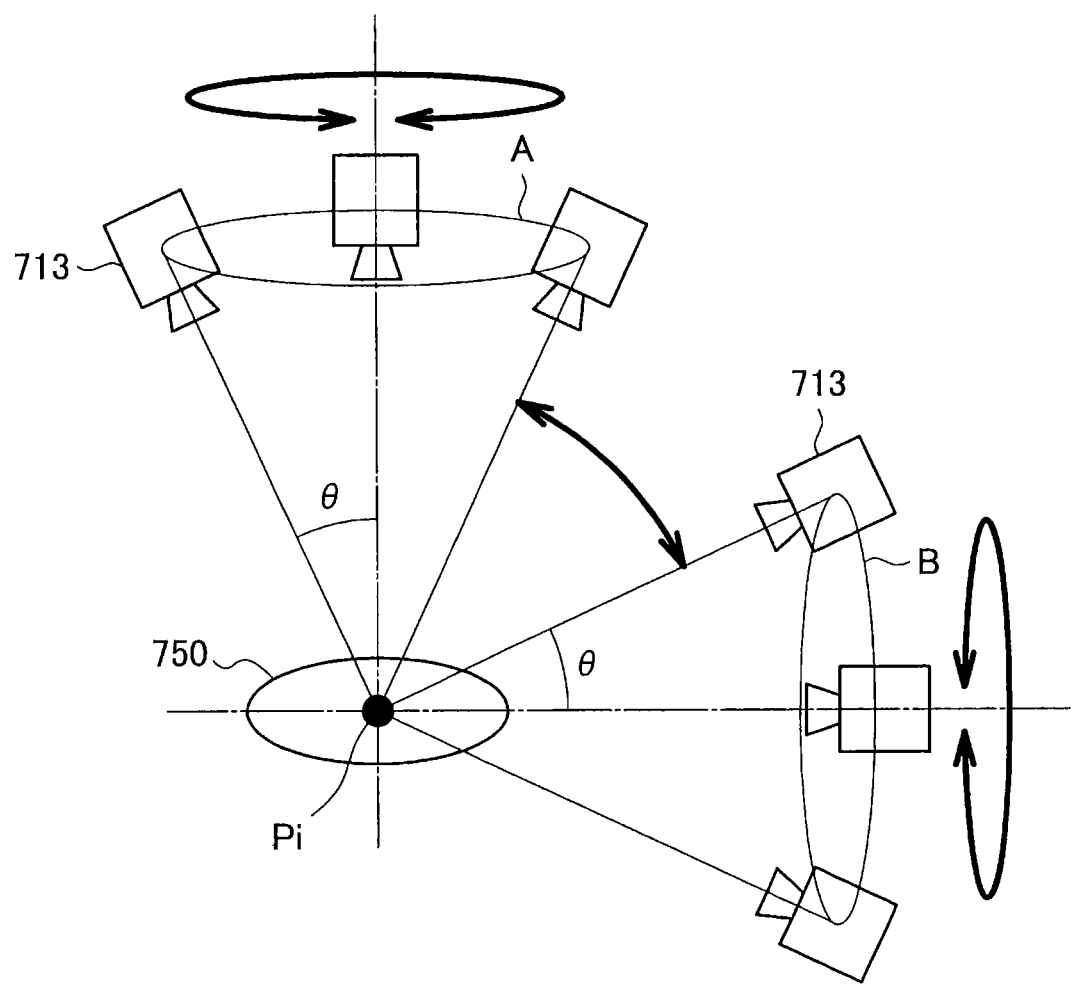
FIG. 7 is an explanatory diagram for describing a pivot movement that is a specific example of an arm movement according to an embodiment of the present disclosure.
Figure 8:
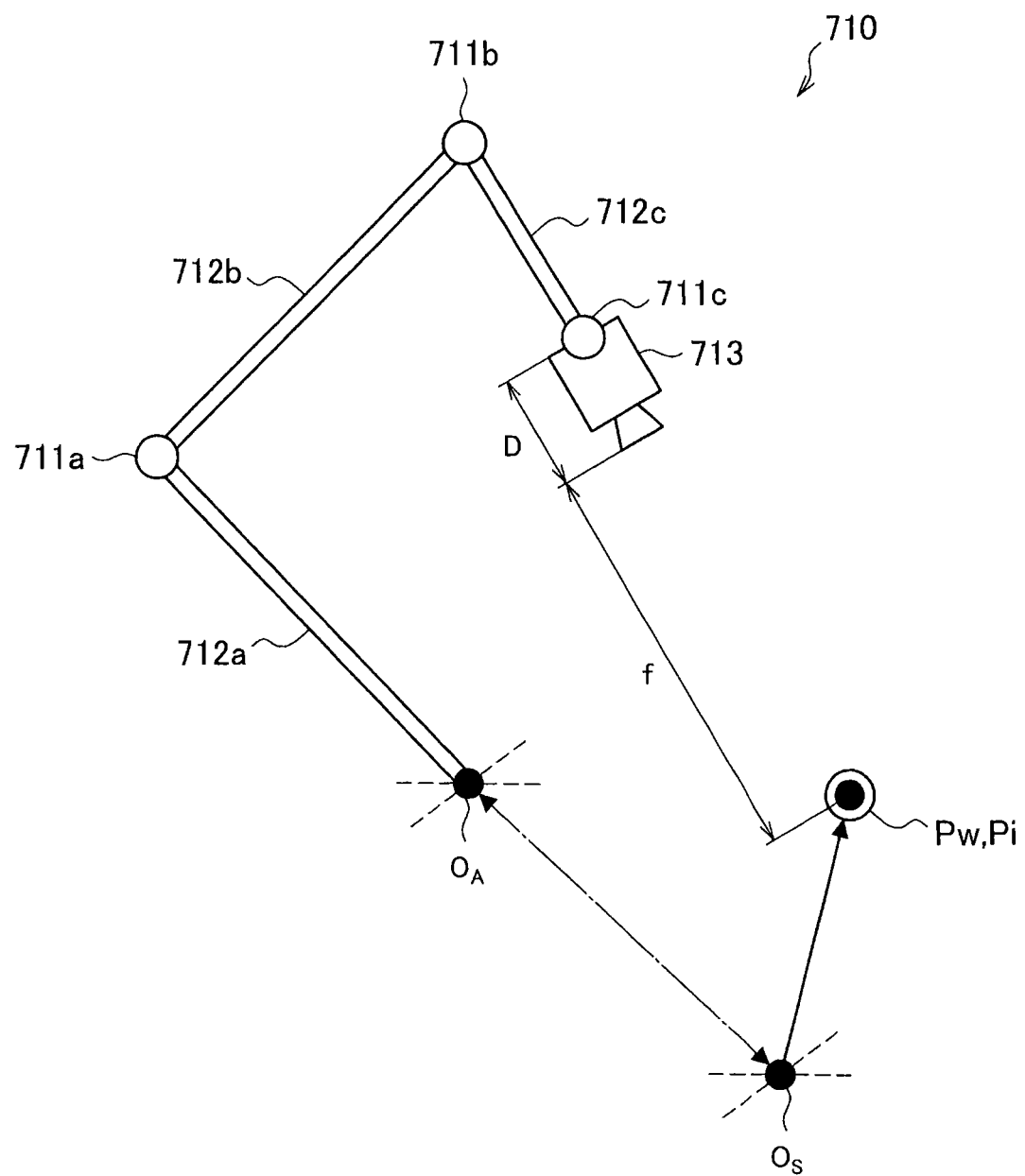
FIG. 8 is an explanatory diagram for describing a purpose of motion and a constraint condition for implementing the pivot movement illustrated in FIG. 7.

The pivot movement will be described in further detail with reference to FIGS. 7 and 8. FIG. 7 is an explanatory diagram for describing the pivot movement that is a specific example of the arm movement according to an embodiment of the present disclosure. FIG. 8 is an explanatory diagram for describing the purpose of motion and the constraint condition for implementing the pivot movement illustrated in FIG. 7.

Referring to FIG. 7, a medical procedure part on a patient 750 is set as an apex in the pivot movement. The apex is referred to as a "pivot point $P_i$." In FIG. 7, for the sake of convenience, in the robot arm apparatus 10 according to the present embodiment, an imaging unit 713 serving as a unit corresponding to the imaging unit 140 of FIG. 6 is illustrated. As illustrated in FIG. 7, in the pivot movement, the purpose of motion and the constraint condition may be set so that the imaging unit 713 can move on a circumference of a bottom of a cone A, that is, the imaging unit 713 moves within a plane of the cone A in a state in which a distance between the imaging unit 713 and the pivot point $P_i$ is maintained constant. Further, the shape of the cone A, that is, an angle θ of an apex of the cone A or a distance between the pivot point $P_i$ and the imaging unit 713, may be appropriately set by the user. For example, the distance between the pivot point $P_i$ and the imaging unit 713 is adjusted to a focal distance of an optical system in the imaging unit 713. As the pivot movement is applied, the medical procedure part can be observed at an equal distance at different angles, and thus convenience for the user who performs surgery can be improved.

Further, in the pivot movement, it is possible to move the position of the cone in which the imaging unit 713 is movable in a state in which the pivot point $P_i$ is fixed as in the cones A and B. In the example illustrated in FIG. 7, the pivot axis of the cone A is substantially perpendicular to the medical procedure part, and the pivot axis of the cone B is substantially parallel to the medical procedure part. As described above, for example, the purpose of motion and the constraint condition may be set so that the cone for performing the pivot movement can be rotated by about 90° in a state in which the pivot point $P_i$ is fixed such as the cones A and B. As the pivot movement is applied, it is possible to observe the medical procedure part from more directions, and thus the convenience for the user can be further improved.

The example illustrated in FIG. 7 illustrates an example in which the purpose of motion and the constraint condition are set so that the imaging unit 713 can move on the circumference of the bottom of the cone A, but the pivot movement according to the present embodiment is not limited to this example. For example, the purpose of motion and the constraint condition may be set so that the distance between the pivot point $P_i$ and the imaging unit 713 can be freely changed in a state in which the position of the pivot point $P_i$ and the angles θ of the apexes of the cones A and B are fixed. As the pivot movement is applied, it is possible to change the distance between the imaging unit 713 and the medical procedure part in a state in which the angle is fixed, and thus it is possible to observe the medical procedure part according to the user's desire, for example, to enlarge or reduce the medical procedure part and then observe the enlarged or reduced medical procedure part by appropriately adjusting the focal distance (focus) of the imaging unit 713.

Next, the purpose of motion and the constraint condition for implementing the pivot movement illustrated in FIG. 7 will be described in detail with reference to FIG. 8. Referring to FIG. 8, an example in which an arm unit 710 including the imaging unit 713 performs the pivot movement using the pivot point $P_i$ as a base point. In FIG. 8, the pivot movement in which the distance between the imaging unit 713 and the pivot point $P_i$ is maintained constant will be described as an example. The arm unit 710 includes a plurality of joint units 711a, 711b, and 711c and a plurality of links 712a, 712b, and 712c, and driving of the arm unit 710 is controlled according to the whole body cooperative control and the ideal joint control according to the present embodiment. For example, the arm unit 710 and the components thereof have the same configurations as the arm unit 420 and the components according to the present embodiment illustrated in FIG. 2.

Here, an arm coordinate system in which an origin $O_A$ serving as a supporting point of the arm unit 710 is used as a zero point and a space coordinate system in which an origin $O_S$ in a space is used as a zero point are considered. The motion of the arm unit 710 is managed by the arm coordinate system. Further, the arm coordinate system and the space coordinate system are defined such that they can be converted into each other.

An imaging center viewed from the space coordinate system is indicated by $P_w$. Further, in the arm coordinate system, a position away from the joint unit 711c connecting the imaging unit 713 with the link 712c by a length D of the imaging unit 713 and a focal distance f of the imaging unit 713 is referred to as a pivot point $P_i$.

In this state, the purpose of motion and the constraint condition are set so that the arm unit 710 is driven in a state in which the pivot point $P_i$ matches the imaging center $P_w$. In other words, the constraint of fixing the pivot point $P_i$ in the arm coordinate system is fixed to the imaging center $P_w$ in the space coordinate system is set in the arm coordinate system. Further, coordinates at which the imaging unit 713 is positioned on the plane of the cone having the pivot point $P_i$ (that is, the imaging center $P_w$) as an apex or the position of the imaging unit 713 at which the imaging unit 713 faces the pivot point $P_i$ is set as the purpose of motion. As the whole body cooperative control is performed under the constraint condition and the purpose of motion, even when the position and posture of the imaging unit 713 are changed by the movement of the arm unit 710, the direction of the imaging unit 713 consistently faces the imaging center $P_w$ (that is, the pivot point $P_i$), and the distance between the imaging unit 713 and the imaging center $P_w$ is maintained to have the focal distance f. Thus, the pivot movement in the state in which the distance between the imaging unit 713 and the imaging center $P_w$ is maintained constant is implemented. When the pivot movement is performed while changing the distance between the imaging unit 713 and the imaging center $P_w$ (or the pivot point $P_i$), it is desirable to change the setting method of the pivot point $P_i$. Specifically, for example, in the arm coordinate system, it is desirable to set the position away from the joint unit 711c by the length D of the imaging unit 713 and an arbitrary distance as the pivot point $P_i$ and use the arbitrary distance a variable parameter.

Further, a combination of the pivot movement and the power assist movement may be used. When a combination of the pivot movement and the power assist movement is used, for example, when the user manually moves the imaging unit 140, the user can move the imaging unit 140 with small power due to a feeling of moving the imaging unit 140 in the non-gravity state, and the moving position of the imaging unit 140 is limited to within the plane of the cone. Thus, the movement operability of the imaging unit 140 is improved at the time of the pivot movement.

The power assist movement and the pivot movement have been described above as the specific example of the purpose of motion according to the present embodiment. The purpose of motion according to the present embodiment is not limited to this example. In the present embodiment, for example, the following purpose of motion can also be implemented.

For example, coordinates of the imaging unit 140 may be set as the purpose of motion so that the position of the imaging unit 140 is fixed at a certain position. In this case, for example, when force is applied from the outside to the components other than the imaging unit 140 of the arm unit 120, it is possible to set the purpose of motion and the constraint condition so that the joint unit 130 and the link are also fixed at a certain position and not moved, and it is possible to set the purpose of motion and the constraint condition so that the joint unit 130 and the link are moved according to the applied external force, but the position of the imaging unit 140 is fixed. In the latter case, for example, when the arm unit 120 interferes with a task and is desired to be moved, control of a high degree of freedom of moving the positions and postures of the other components of the arm unit 120 in the state in which an image captured by the imaging unit 140 is fixed is implemented.

Further, the purpose of motion and the constraint condition may be set so that a movement of stopping driving of the arm unit 120 immediately is implemented, for example, when the arm unit 120 detects contact with a person or a thing while being driven. By performing such a movement, it is possible to reduce a risk of the arm unit 120 colliding with a person or object. Further, when the arm unit 120 comes into contact with a person or object, for example, the joint state detecting unit 132 may detect the contact according to a change in the external torque applied to the joint unit 130.

Further, for example, the purpose of motion may be set so that the imaging unit 140 moves along a certain trajectory in the space. Specifically, coordinates of points indicating the certain trajectory may be set as the purpose of motion. By setting the purpose of motion as described above, the movable range of the imaging unit 140 is limited to the trajectory. Further, by setting the speed of the imaging unit 140, times at which the imaging unit 140 passes through the points, or the like as the purpose of motion together with the coordinates of the points indicating the trajectory, automated driving by which the imaging unit 140 automatically moves along a certain trajectory at a certain timing can also be performed. The driving control according to such a motion setting is effective, for example, when the robot arm apparatus 10 repeatedly performs a certain task automatically.

Further, for example, the purpose of motion and the constraint condition may be set so that a movement of preventing the arm unit 120 from invading a certain region in the space is implemented. As described above with reference to FIG. 1, in the present embodiment, the user performs surgery while viewing the display screen. Thus, if the arm unit 120 is positioned in a region between the user and the display screen, the user's field of vision is blocked, and thus the surgery efficiency is likely to be lowered. Thus, for example, by setting the region between the user and the display screen as an invasion prohibition region of the arm unit 120, the surgery efficiency can be improved.

Here, when the invasion prohibition region is set to the arm unit 120 as described above, it is preferable that the degrees of freedom of the arm unit 120 be more than the 6 degrees of freedom. This is because degrees of freedom after the 6 degrees of freedom can be used as redundant degrees of freedom, and thus it is possible to secure driving of the 6 degrees of freedom while dealing with the invasion prohibition region or the like. A configuration of a robot arm apparatus including an arm unit having more degrees of freedom than the 6 degrees of freedom will be described in detail with reference to FIG. 9.

Figure 9:
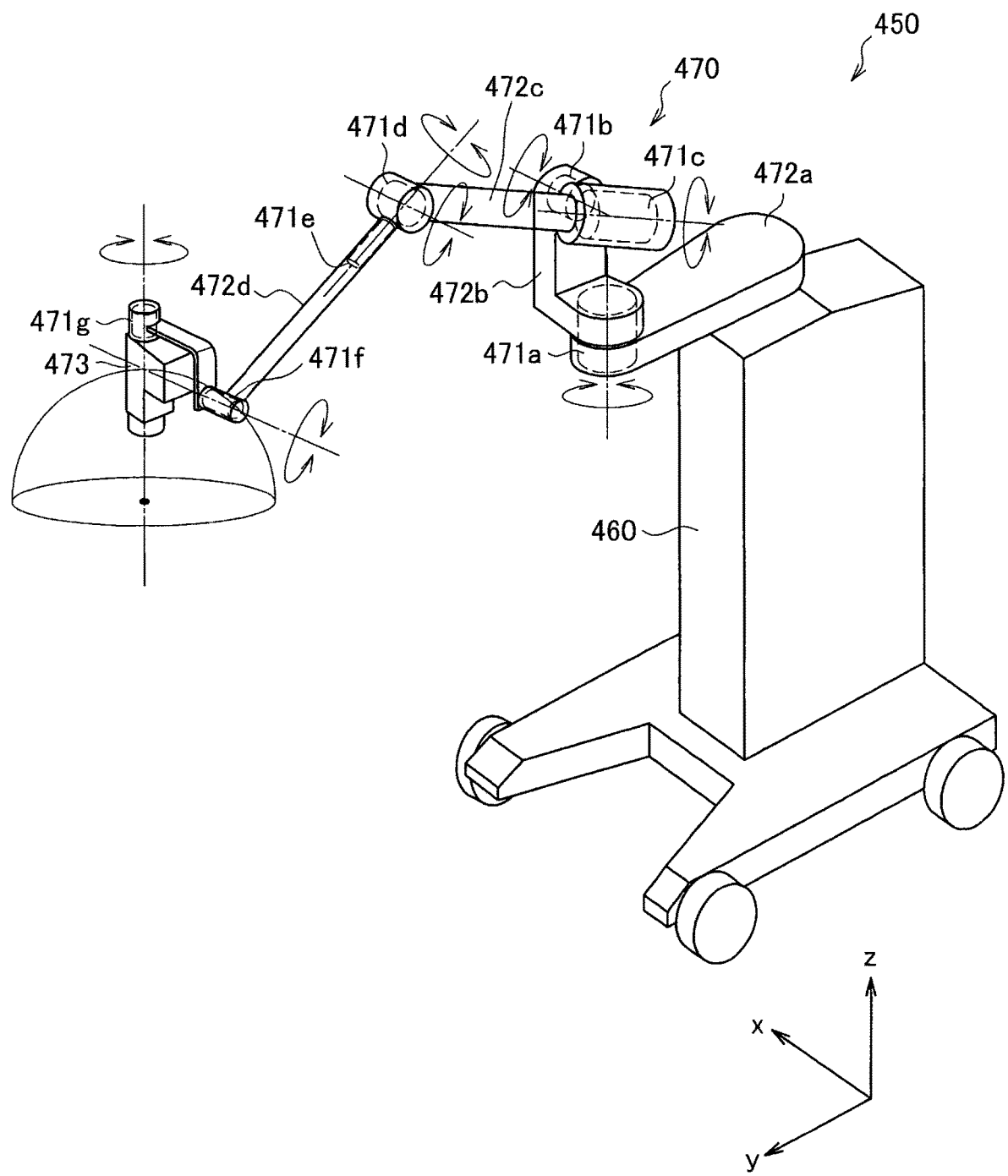
FIG. 9 is a schematic diagram illustrating an external appearance of a modified example having a redundant degree of freedom in a robot arm apparatus according to an embodiment of the present disclosure.

FIG. 9 is a schematic diagram illustrating an external appearance of a modified example having a redundant degree of freedom in a robot arm apparatus according to an embodiment of the present disclosure. The same coordinate axes as the directions defined in FIG. 2 are illustrated in FIG. 9.

Referring to FIG. 9, a robot arm apparatus 450 according to the present modified example includes a base unit 460 and an arm unit 470. Further, the arm unit 470 includes a plurality of joint units 471a to 471g, a plurality of links 472a to 472d connecting the joint units 471a to 471g with one another, and an imaging unit 473 installed at the front edge of the arm unit 470. Here, the robot arm apparatus 450 illustrated in FIG. 9 corresponds to a configuration in which the degrees of freedom of the arm unit 470 are increased by one compared to the robot arm apparatus 400 described above with reference to FIG. 2. Thus, the functions and configurations of the base unit 460, each of the joint units 471a to 471g and the links 472a to 472d, and the imaging unit 473 are similar to the functions and configurations of the base unit 410, each of the joint units 421a to 421f and the links 422a to 422c, and the imaging unit 423 of the robot arm apparatus 400 described above with reference to FIG. 2, and thus a detailed description thereof is omitted. The following description will proceed focusing on a configuration of the arm unit 470 serving as a difference with the robot arm apparatus 400.

The robot arm apparatus 450 according to the present embodiment includes the 7 joint units 471a to 471g, and 7 degrees of freedom are implemented with regard to driving of the arm unit 470. Specifically, one end of the link 472a is connected with the base unit 460, and the other end of the link 472a is connected with one end of the link 472b through the joint unit 421a. Further, the other end of the link 422b is connected with one end of the link 472c through the joint units 471b and 471c. Furthermore, the other end of the link 472c is connected with one end of the link 472d through the joint units 471d and 471e, and the other end of 472d is connected with the imaging unit 473 through the joint units 471f and 471g. As described above, the arm unit 470 extending from the base unit 460 is configured such that the base unit 460 serves as a support point, and the ends of the plurality of links 472a to 472d are connected with one another through the joint units 471a to 471g.

Further, as illustrated in FIG. 9, the joint units 471a, 471c, 471e, and 471g are installed such that the long axis direction of the links 472b to 472d connected thereto and the photographing direction of the imaging unit 473 connected thereto are set as the rotary axis direction, and the joint units 471b, 471d, and 471f are installed such that the x axis direction serving as a direction in which connection angles of the links 472c and 472d and the imaging unit 473 connected thereto are changed within the y-z plane is set as the rotary axis direction. As described above, in the present modified example, the joint units 471a, 471c, 471e, and 471g have a function of performing yawing, and the joint units 471b, 471d, and 471f have a function of performing pitching.

As the arm unit 470 has the above configuration, in the robot arm apparatus 450 according to the present embodiment, the 7 degrees of freedom are implemented with regard to driving of the arm unit 470, and thus it is possible to freely move the imaging unit 473 within the space in the movable range of the arm unit 470, and the redundant degree of freedom is provided. In FIG. 9, similarly to FIG. 2, a hemisphere is illustrated as an example of the movable range of the imaging unit 473. When the central point of the hemisphere is the photographing center of the medical procedure part photographed by the imaging unit 473, the medical procedure part can be photographed at various angles by moving the imaging unit 473 on the spherical surface of the hemisphere in a state in which the photographing center of the imaging unit 473 is fixed to the central point of the hemisphere. Since the robot arm apparatus 450 according to the present embodiment has one redundant degree of freedom, it is possible to limit the movement of the imaging unit 473 to the hemisphere and the trajectory of the arm unit 470, and it is also possible to easily deal with the constraint condition such as the invasion prohibition region. By setting the invasion prohibition region, for example, it is possible to control driving of the arm unit 470 so that the arm unit 470 is not positioned between the monitor on which the image captured by the imaging unit 473 is displayed and the practitioner or the staff, and it is possible to prevent the monitor from being blocked from the view of the practitioner and the staff. Further, as the invasion prohibition region is set, it is possible to control driving of the arm unit 470 so that the arm unit 470 moves while avoiding interference (contact) with the practitioner and the staff or any other device therearound.

<3. Processing Procedure of Robot Arm Control Method>

Figure 10:
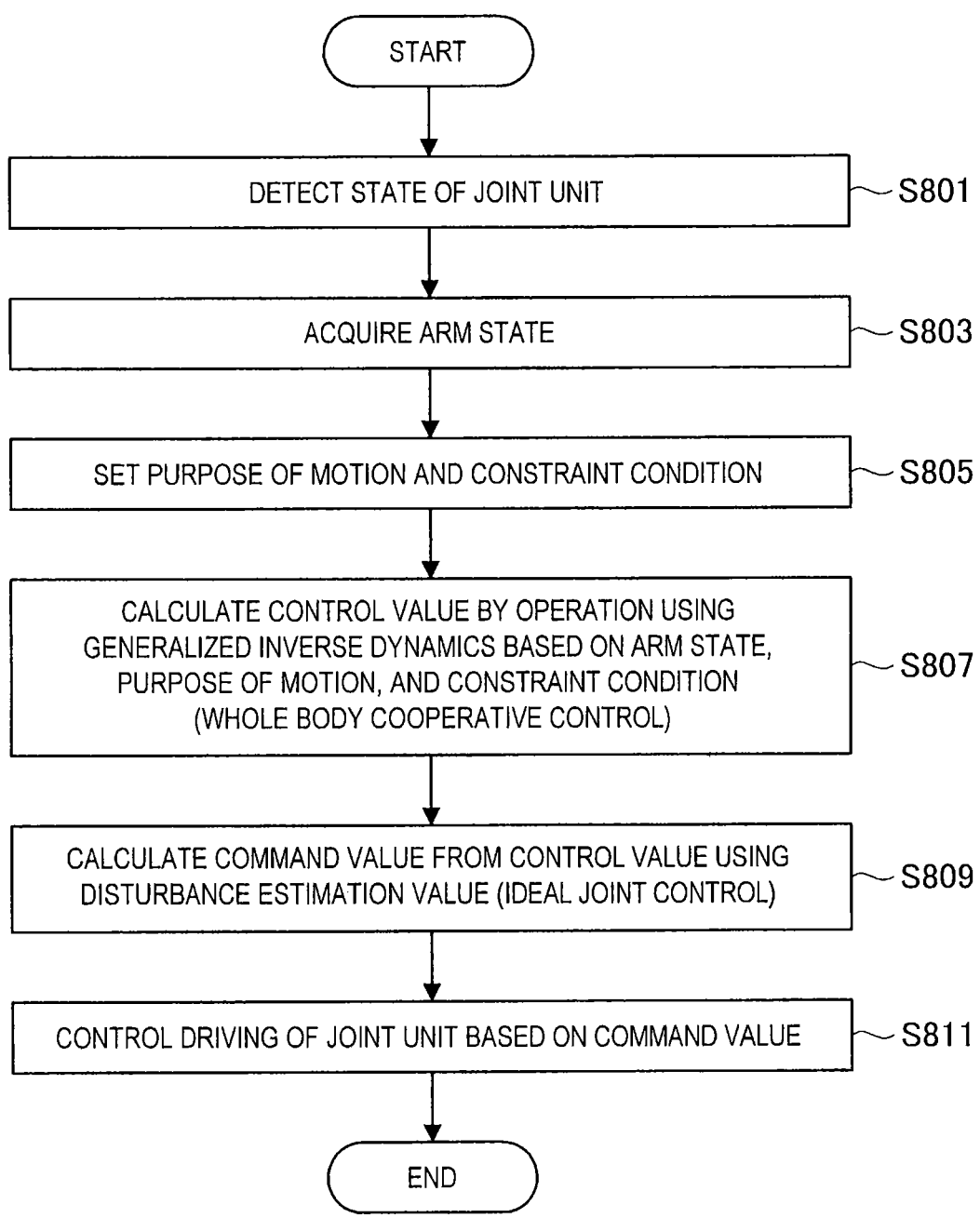
FIG. 10 is a flowchart illustrating a processing procedure of a robot arm control method according to an embodiment of the present disclosure.

Next, a processing procedure of a robot arm control method according to an embodiment of the present disclosure will be described with reference to FIG. 10. FIG. 10 is a flowchart illustrating a processing procedure of a robot arm control method according to an embodiment of the present disclosure. The following description will proceed with an example in which the robot arm control method according to the present embodiment is implemented through the configuration of the robot arm control system 1 illustrated in FIG. 6. Thus, the robot arm control method according to the present embodiment may be a medical robot arm control method. Further, in the following description of the processing procedure of the robot arm control method according to the present embodiment, the functions of the respective components of the robot arm control system 1 illustrated in FIG. 6 have already been described above in [2-4. Configuration of the robot arm control system], and thus a detailed description thereof is omitted.

Referring to FIG. 10, in the robot arm control method according to the present embodiment, first, in step S801, the joint state detecting unit 132 detects the state of the joint unit 130. Here, the state of the joint unit 130 refers to, for example, the rotational angle, the generated torque and/or the external torque in the joint unit 130.

Then, in step S803, the arm state acquiring unit 241 acquires the arm state based on the state of the joint unit 130 detected in step S801. The arm state refers to a motion state of the arm unit 120, and may be, for example, a position, a speed, or acceleration of each component of the arm unit 120, or force acting on each component of the arm unit 120.

Then, in step S805, the operation condition setting unit 242 sets the purpose of motion and the constraint condition used for the operation in the whole body cooperative control based on the arm state acquired in step S803. Further, the operation condition setting unit 242 may not set the purpose of motion based on the arm state, may set the purpose of motion based on the instruction information on driving of the arm unit 120 which is input, for example, from the input unit 210 by the user, and may use the purpose of motion previously stored in the storage unit 220. Furthermore, the purpose of motion may be set by appropriately combining the above methods. Moreover, the operation condition setting unit 242 may use the constraint condition previously stored in the storage unit 220.

Then, in step S807, the operation for the whole body cooperative control using the generalized inverse dynamics is performed based on the arm state, the purpose of motion, and the constraint condition, and a control value $\tau_a$ is calculated. The process performed in step S807 may be a series of processes in the virtual force calculating unit 243 and the actual force calculating unit 244 illustrated in FIG. 6, that is, a series of processes described above in [2-2. Generalized inverse dynamics].

Then, in step S809, the disturbance estimation value $\tau_d$ is calculated, the operation for the ideal joint control is performed using the disturbance estimation value $\tau_d$, and the command value $\tau$ is calculated based on the control value $\tau_a$. The process performed in step S809 may be a series of processes in the ideal joint control unit 250 illustrated in FIG. 6, that is, a series of processes described above in [2-3. Ideal joint control].

Lastly, in step S811, the drive control unit 111 controls driving of the joint unit 130 based on the command value $\tau$.

The processing procedure of the robot arm control method according to the present embodiment has been described above with reference to FIG. 10. In the present embodiment, the process of step S801 to step S811 illustrated in FIG. 10 is repeatedly performed while the task using the arm unit 120 is being performed. Thus, in the present embodiment, driving control of the arm unit 120 is continuously performed while the task using the arm unit 120 is being performed.

<4. Hardware Configuration>

Next, a hardware configuration of the robot arm apparatus 10 and the control device 20 according to the present embodiment illustrated in FIG. 6 will be described in detail with reference to FIG. 11. FIG. 11 is a functional block diagram illustrating an exemplary configuration of a hardware configuration of the robot arm apparatus 10 and the control device 20 according to an embodiment of the present disclosure.

The robot arm apparatus 10 and the control device 20 mainly include a CPU 901, a ROM 903, and a RAM 905. The robot arm apparatus 10 and the control device 20 further include a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device, and controls all or some operations of the robot arm apparatus 10 and the control device 20 according to various kinds of programs recorded in the ROM 903, the RAM 905, the storage device 919, or a removable storage medium 927. The ROM 903 stores a program, an operation parameter, or the like used by the CPU 901. The RAM 905 primarily stores a program used by the CPU 901, a parameter that appropriately changes in execution of a program, or the like. The above-mentioned components are connected with one another by the host bus 907 configured with an internal bus such as a CPU bus. The CPU 901 corresponds to, for example, the arm control unit 110 and the control unit 230 illustrated in FIG. 6 in the present embodiment.

The host bus 907 is connected to the external bus 911 such as a peripheral component interconnect/interface (PCI) bus through the bridge 909. Further, the input device 915, the output device 917, the storage device 919, the drive 921, the connection port 923, and the communication device 925 are connected to the external bus 911 via the interface 913.

The input device 915 is an operating unit used by the user such as a mouse, a keyboard, a touch panel, a button, a switch, a lever, or a pedal. For example, the input device 915 may be a remote control unit (a so-called remote controller) using infrared light or any other radio waves, and may be an external connection device 929 such as a mobile telephone or a PDA corresponding to an operation of the robot arm apparatus 10 and the control device 20. Further, for example, the input device 915 is configured with an input control circuit that generates an input signal based on information input by the user using the operating unit, and outputs the input signal to the CPU 901. The user of the robot arm apparatus 10 and the control device 20 can input various kinds of data to the robot arm apparatus 10 and the control device 20 or instruct the robot arm apparatus 10 and the control device 20 to perform a processing operation by operating the input device 915. For example, the input device 915 corresponds to the input unit 210 illustrated in FIG. 6 in the present embodiment. Further, in the present embodiment, the purpose of motion in driving of the arm unit 120 may be set by an operation input through the input device 915 by the user, and the whole body cooperative control may be performed according to the purpose of motion.

The output device 917 is configured with a device capable of visually or acoustically notifying the user of the acquired information. As such a device, there are a display device such as a CRT display device, a liquid crystal display device, a plasma display device, an EL display device or a lamp, an audio output device such as a speaker or a headphone, a printer device, and the like. For example, the output device 917 outputs a result obtained by various kinds of processes performed by the robot arm apparatus 10 and the control device 20. Specifically, the display device displays a result obtained by various kinds of processes performed by the robot arm apparatus 10 and the control device 20 in the form of text or an image. Meanwhile, the audio output device converts an audio signal including reproduced audio data, acoustic data, or the like into an analogue signal, and outputs the analogue signal. In the present embodiment, various kinds of information related to driving control of the arm unit 120 may be output from the output device 917 in all forms. For example, in driving control of the arm unit 120, the trajectory of movement of each component of the arm unit 120 may be displayed on the display screen of the output device 917 in the form of a graph. Further, for example, the display device 30 illustrated in FIG. 6 may be a device including the function and configuration of the output device 917 serving as the display device and a component such as a control unit for controlling driving of the display device.

The storage device 919 is a data storage device configured as an exemplary storage unit of the robot arm apparatus 10 and the control device 20. For example, the storage device 919 is configured with a magnetic storage unit device such as a hard disk drive (HDD), a semiconductor storage device, an optical storage device, a magneto optical storage device, or the like. The storage device 919 stores a program executed by the CPU 901, various kinds of data, and the like. For example, the storage device 919 corresponds to the storage unit 220 illustrated in FIG. 6 in the present embodiment. Further, in the present embodiment, the storage device 919 may store the operation condition (the purpose of motion and the constraint condition) in the operation related to the whole body cooperative control using the generalized inverse dynamics, and the robot arm apparatus 10 and the control device 20 may perform the operation related to the whole body cooperative control using the operation condition stored in the storage device 919.

The drive 921 is a recording medium reader/writer, and is equipped in or attached to the robot arm apparatus 10 and the control device 20. The drive 921 reads information stored in the removable storage medium 927 mounted thereon such as a magnetic disk, an optical disc, a magneto optical disc, or a semiconductor memory, and outputs the read information to the RAM 905. Further, the drive 921 can write a record in the removable storage medium 927 mounted thereon such as a magnetic disk, an optical disk, a magneto optical disk, or a semiconductor memory. For example, the removable storage medium 927 is a DVD medium, an HD-DVD medium, a Blu-ray (a registered trademark) medium, or the like. Further, the removable storage medium 927 may be a Compact Flash (CF) (a registered trademark), a flash memory, a Secure Digital (SD) memory card, or the like. Furthermore, for example, the removable storage medium 927 may be an integrated circuit (IC) card equipped with a non-contact type IC chip, an electronic device, or the like. In the present embodiment, various kinds of information related to driving control of the arm unit 120 is read from various kinds of removable storage media 927 or written in various kinds of removable storage media 927 through the drive 921.

The connection port 923 is a port for connecting a device directly with the robot arm apparatus 10 and the control device 20. As an example of the connection port 923, there are a Universal Serial Bus (USB) port, an IEEE1394 port, a Small Computer System Interface (SCSI) port, and the like. As another example of the connection port 923, there are an RS-232C port, an optical audio terminal, a High-Definition Multimedia Interface (HDMI) (a registered trademark), and the like. As the external connection device 929 is connected to the connection port 923, the robot arm apparatus 10 and the control device 20 acquire various kinds of data directly from the external connection device 929 or provide various kinds of data to the external connection device 929. In the present embodiment, various kinds of information related to driving control of the arm unit 120 may be read from various kinds of external connection devices 929 or written in various kinds of external connection devices 929 through the connection port 923.

For example, the communication device 925 is a communication interface configured with a communication device used for a connection with a communication network (network) 931. For example, the communication device 925 is a communication card for a wired or wireless local area network (LAN), Bluetooth (a registered trademark), or wireless USB (WUSB). Further, the communication device 925 may be an optical communication router, an asymmetric digital subscriber line (ADSL) router, various kinds of communication modems, or the like. For example, the communication device 925 can transmit or receive a signal to or from the Internet or another communication device, for example, according to a certain protocol such as TCP/IP. Further, the communication network 931 connected to the communication device 925 is configured with a network connected in a wired or wireless manner, and may be, for example, the Internet, a domestic LAN, infrared ray communication, radio wave communication, satellite communication, or the like. In the present embodiment, various kinds of information related to driving control of the arm unit 120 may be transmitted or received to or from an external device via the communication network 931 through the communication device 925.

The hardware configuration capable of implementing the functions of the robot arm apparatus 10 and the control device 20 according to an embodiment of the present disclosure has been described above. Each of the above components may be configured using a versatile member, and may be configured by hardware specialized for the function of each component. Thus, the hardware configuration to be used may be appropriately changed according to a technology level when the present embodiment is carried out. Further, although not illustrated in FIG. 11, the robot arm apparatus 10 obviously includes various kinds of components corresponding to the arm unit 120 illustrated in FIG. 6.

Further, it is possible to create a computer program for implementing the functions of the robot arm apparatus 10 according to the present embodiment, the control device 20, and the display device 30 and install the computer program in a personal computer or the like. Furthermore, it is possible to provide a computer readable recording medium storing the computer program as well. Examples of the recording medium include a magnetic disk, an optical disc, a magneto optical disc, and a flash memory. Further, for example, the computer program may be delivered via a network without using the recording medium.

<5. Conclusion>

As described above, in the present embodiment, the following effects can be obtained.

As described above, according to the present embodiment, the arm unit 120 having the multi-link structure in the robot arm apparatus 10 has at least 6 or more degrees of freedom, and driving of each of the plurality of joint units 130 configuring the arm unit 120 is controlled by the drive control unit 111. Further, the medical apparatus is installed at the front edge of the arm unit 120. As driving of each joint unit 130 is controlled as described above, driving control of the arm unit 120 having a high degree of freedom is implemented, and the robot arm apparatus 10 for medical use having high operability for a user is implemented.

Specifically, according to the present embodiment, in the robot arm apparatus 10, the state of the joint unit 130 is detected by the joint state detecting unit 132. Further, in the control device 20, based on the state of the joint unit 130, the purpose of motion, and the constraint condition, various kinds of operations related to the whole body cooperative control using the generalized inverse dynamics for controlling driving of the arm unit 120 are performed, and torque command value τ serving as the operation result are calculated. Furthermore, in the robot arm apparatus 10, driving of the arm unit 120 is controlled based on the torque command value τ. As described above, in the present embodiment, driving of the arm unit 120 is controlled by the whole body cooperative control using the generalized inverse dynamics. Thus, driving control of the arm unit 120 according to the force control is implemented, and the robot arm apparatus having the high operability for the user is implemented. Further, in the present embodiment, in the whole body cooperative control, for example, control for implementing various kinds of purposes of motion for improving user convenience such as the pivot movement and the power assist movement can be performed. Furthermore, in the present embodiment, for example, various driving units for moving the arm unit 120 manually or through an operation input from a pedal are implemented, and thus user convenience is further improved.

Further, in the present embodiment, the whole body cooperative control and the ideal joint control are applied to driving control of the arm unit 120. In the ideal joint control, a disturbance component such as friction or inertia in the joint unit 130 is estimated, and feedforward control is performed using the estimated disturbance component. Thus, even when there is a disturbance component such as friction, the ideal response can be implemented on driving of the joint unit 130. Thus, small influence of vibration or the like, high-accuracy responsiveness, and high positioning accuracy or stability are implemented in driving control of the arm unit 120.

Further, in the present embodiment, each of the plurality of joint units 130 configuring the arm unit 120 has a configuration suitable for the ideal joint control illustrated in FIG. 3, for example, and the rotational angle, the generated torque and the viscous drag coefficient of each of the joint units 130 can be controlled according to an electric current value. As described above, driving of each of the joint units 130 is controlled according to an electric current value, and driving of each of the joint units 130 is controlled according to the whole body cooperative control while detecting the entire state of the arm unit 120, and thus the counter balance is unnecessary, and the small robot arm apparatus 10 is implemented.

As described above, according to the present embodiment, it is possible to fulfill all capabilities necessary for the robot arm apparatus described above in <1. Review of medical robot arm apparatus>. Thus, it is possible to perform various kinds of medical procedures more efficiently using the robot arm apparatus according to the present embodiment and further reduce the fatigue or the burden of the user or the patient.

Further, in the present embodiment, as the arm unit 120 of the robot arm apparatus 10 is driven by the force control, even when the arm unit 120 interferes with or comes into contact with the practitioner, the staff, or the like during driving, the arm unit 120 does not generate larger force than necessary, and the arm unit 120 safely stops. Furthermore, when the interference is resolved, the arm unit 120 is moved up to a desired position according to the set purpose of motion, and the medical procedure is continued. As described above, in the present embodiment, as the force control is used for driving control of the robot arm apparatus 10, higher safety is secured even when the arm unit 120 interferes with something nearby while being driven.

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

For example, the above embodiment has shown an example in which a front edge unit of an arm unit of a robot arm apparatus is an imaging unit, and a medical procedure part is photographed by the imaging unit during surgery as illustrated in FIG. 1, but the present embodiment is not limited to this example. The robot arm control system 1 according to the present embodiment can be applied even when a robot arm apparatus including a different front edge unit is used for another purpose. For example, the front edge unit may be an endoscope or a laparoscope (and a treatment tool), and may be any other examination device such as an ultrasonic examination apparatus or a gastrocamera.

For example, in a medical procedure using a laparoscope, a medical procedure method of inserting a plurality of treatment tools and a laparoscope into the patient's body at different angles and performing various kinds of treatments using the treatment tools while observing the medical procedure part through the laparoscope is performed. In this medical procedure method, for example, when the practitioner can operate the treatment tool while operating the laparoscope used to observe the medical procedure part through the robot arm, a single user can perform the medical procedure, and the medical procedure can be performed more efficiently. With the operability of the existing general balance arms, it is difficult for a single user to perform an operation of the treatment tool with his/her hand and an operation of the laparoscope through the balance arm at the same time. Thus, in the existing method, commonly, a plurality of staffs are necessary, and one practitioner performs a treatment while operating the treatment tool, and the other person operates the observation laparoscope. However, in the robot arm apparatus according to the present embodiment, high operability is implemented by the whole body cooperative control as described above. Further, little influence of vibration or the like, the high-accuracy responsiveness, and the high stability are implemented by the ideal joint control. Thus, for example, since the observation laparoscope is operated through the robot arm apparatus according to the present embodiment, one practitioner can easily perform the operation of the treatment tool with his/her hand and the operation of the observation laparoscope by the robot arm apparatus.

Further, the robot arm apparatus according to the present embodiment may be used for purposes other than medical uses. In the robot arm apparatus according to the present embodiment, since the high-accuracy responsiveness and the high stability are implemented through the ideal joint control, for example, it is also possible to deal with a task such as processing or assembly of industrial components that has to be performed with a high degree of accuracy.

Further, the above embodiment has been described in connection with the example in which the joint unit of the robot arm apparatus includes a rotation mechanism, and rotary driving of the rotation mechanism is controlled such that driving of the arm unit is controlled, but the present embodiment is not limited to this example. For example, in the robot arm apparatus according to the present embodiment, the link configuring the arm unit may have a mechanism that expands or contracts in an extension direction of the link, and the length of the link may be variable. When the length of the link is variable, for example, driving of the arm unit is controlled such that a desired purpose of motion is achieved by the whole body cooperative control in which expansion and contraction of the link is considered in addition to rotation in the joint unit.

Further, the above embodiment has been described in connection with the example in which the degrees of freedom of the arm unit in the robot arm apparatus are the 6 or more degrees of freedom, but the present embodiment is not limited to this example. Further, the description has proceeded with the example in which each of the plurality of joint units configuring the arm unit includes the actuator that supports the ideal joint control, but the present embodiment is not limited to this example. In the present embodiment, various purposes of motion can be set according to the purpose of the robot arm apparatus. Thus, as long as the set purpose of motion can be achieved, the arm unit may have fewer than 6 degrees of freedom, and some of the plurality of joint units configuring the arm unit may be joint units having a general joint mechanism. As described above, in the present embodiment, the arm unit may be configured to be able to achieve the purpose of motion or may be appropriately configured according to the purpose of the robot arm apparatus.

Additionally, the present technology may also be configured as below.

(1)

A medical robot arm apparatus including:

a plurality of joint units configured to connect a plurality of links and implement at least 6 or more degrees of freedom in driving of a multi-link structure configured with the plurality of links; and a drive control unit configured to control driving of the joint units based on states of the joint units, wherein a front edge unit attached to a front edge of the multi-link structure is at least one medical apparatus.

(2)

The medical robot arm apparatus according to (1), wherein the drive control unit controls the driving of the joint units based on a control value for whole body cooperative control of the multi-link structure calculated according to generalized inverse dynamics using a state of the multi-link structure acquired based on the detected states of the plurality of joint units and a purpose of motion and a constraint condition of the multi-link structure.

(3)

The medical robot arm apparatus according to (2), wherein the control value is calculated based on virtual force serving as virtual force acting to achieve the purpose of motion in an operation space describing a relation between force acting on the multi-link structure and acceleration generated in the multi-link structure and actual force obtained by converting the virtual force into actual force for driving the joint units based on the constraint condition.

(4)

The medical robot arm apparatus according to (2) or (3), wherein the drive control unit controls the driving of the joint units based on a command value for implementing an ideal response of the multi-link structure which is calculated by correcting influence of a disturbance on the control value.

(5)

The medical robot arm apparatus according to (4), wherein the command value is calculated by correcting the control value using a disturbance estimation value indicating influence of a disturbance on the driving of the joint units estimated based on the detected states of the joint units.

(6)

The medical robot arm apparatus according to any one of (2) to (5), wherein the purpose of motion is at least a power assist movement of controlling the states of the joint units such that gravity acting on the multi-link structure is negated and controlling the states of the joint units such that movement of the multi-link structure in a direction of force further applied from an outside is supported.

(7)

The medical robot arm apparatus according to any one of (2) to (6), wherein the purpose of motion is a turning movement in which a front edge unit installed at a front edge of an arm serving as the multi-link structure moves on a plane of a cone having a certain point as an apex in a state in which a direction of the front edge unit is fixed on a certain point in a space, and an axis of the cone is used as a pivot axis.

(8)

The medical robot arm apparatus according to (7), wherein, in the turning movement, a distance between the front edge unit and the certain point is maintained constant.

(9)

The medical robot arm apparatus according to any one of (2) to (6), wherein the front edge unit is an imaging unit configured to be installed at a front edge of an arm serving as the multi-link structure and acquire an image of a photographing target, and the purpose of motion is a turning movement in which the imaging unit moves on a plane of a cone having a certain point as an apex in a state in which a photographing direction of the imaging unit is fixed on a certain point in a space, and an axis of the cone is used as a pivot axis.

(10)

The medical robot arm apparatus according to (9), wherein, in the turning movement, a distance between the imaging unit and the certain point is maintained constant.

(11)

The medical robot arm apparatus according to any one of (1) to (10), wherein each of the plurality of joint units includes a joint state detecting unit configured to detect the state of the joint unit, and wherein the joint state detecting unit includes at least a torque detecting unit configured to detect generated torque of the joint units and external torque applied to the joint unit from an outside, and a rotational angle detecting unit configured to detect a rotational angle of the joint unit.

(12)

The medical robot arm apparatus according to (4) or (5), wherein the control value and the command value are generated torque of the joint unit.

(13)

A medical robot arm control system including:

a medical robot arm apparatus including a plurality of joint units configured to connect a plurality of links and implement at least 6 or more degrees of freedom with respect to a multi-link structure configured with the plurality of links, and a drive control unit that controls driving of the joint units based on detected states of the plurality of joint units, wherein a front edge unit attached to a front edge of the multi-link structure is at least one medical apparatus; and a control device including a whole body cooperative control unit configured to calculate a control value for whole body cooperative control of the multi-link structure according to generalized inverse dynamics using a state of the multi-link structure acquired based on the detected states of the plurality of joint units and a purpose of motion and a constraint condition of the multi-link structure.

(14)

A medical robot arm control method including:

detecting states of a plurality of joint units configured to connect a plurality of links and implement at least 6 or more degrees of freedom with respect to a multi-link structure configured with the plurality of links; and controlling driving of the joint units based on the detected states of the plurality of joint units, wherein a front edge unit attached to a front edge of the multi-link structure is at least one medical apparatus.

(15)

A program for causing a computer to execute:

a function of detecting states of a plurality of joint units configured to connect a plurality of links and implement at least 6 or more degrees of freedom with respect to a multi-link structure configured with the plurality of links; and a function of controlling driving of the joint units based on the detected states of the plurality of joint units, wherein a front edge unit attached to a front edge of the multi-link structure is at least one medical apparatus.

(16)

A surgical imaging apparatus comprising:

a multi-link, multi-joint structure including a plurality of joints that interconnect a plurality of links to provide the multi-link, multi-joint structure with a plurality of degrees of freedom, at least one video camera being disposed on a distal end of the multi-link, multi-joint structure;

at least one actuator that drives at least one of the plurality of joints; and circuitry configured to:

detect a joint force experienced at the at least one of the plurality of joints in response to an applied external force, and control the at least one actuator based on the joint force so as to position the video camera.

(17)

The surgical imaging apparatus according to (16), wherein the joint force includes a direct force, which is applied directly to the at least one of the joints, and an indirect force, which is applied directly to another of the joints and applied indirectly to the at least one of the joints.

(18)

The surgical imaging apparatus according to (16), wherein the applied external force is applied to at least a link or a joint of the multi-link, multi-joint structure, or the video camera.

(19)

The surgical imaging apparatus according to (18), wherein the applied external force is based on a force applied by user to the video camera.

(20)

The surgical imaging apparatus according to (16), wherein the circuitry controls the at least one actuator to move the video camera in a direction of the applied external force.

(21)

The surgical imaging apparatus according to (16), wherein the circuitry controls the at least one actuator to move the video camera such that a field of view of the video camera is adjusted.

(22)

The surgical imaging apparatus according to (16), wherein the circuitry controls a movement speed of the video camera based on a magnitude of the applied external force.

(23)

The surgical imaging apparatus according to (16), wherein the circuitry controls the video camera to autofocus an image captured by the video camera.

(24)

The surgical imaging apparatus according to (16), wherein the circuitry controls the video camera to autofocus during a movement of the video camera.

(25)

The surgical imaging apparatus according to (16), further comprising at least one sensor that detects the joint force, the sensor being disposed at the at least one of the plurality of joints, wherein the circuitry detects the joint force based on a signal output by the sensor.

(26)

The surgical imaging apparatus according to (16), wherein the video camera includes two imagers that capture a three-dimensional (3D) image.

(27)

The surgical imaging apparatus according to (26), wherein the circuitry digitally magnifies and reduces the 3D image (28)

The surgical imaging apparatus according to (26), wherein the circuitry controls the video camera to optically magnify and reduce the 3D image.

(29)

The surgical imaging apparatus according to (16), wherein the circuitry controls the at least one actuator such that a position of the video camera is stabilized.

(30)

The surgical imaging apparatus according to (29), wherein the circuitry controls the at least one actuator to unlock the stabilized video camera in response to an input.

(31)

The surgical imaging apparatus according to (16), wherein the circuitry controls the at least one actuator such that a viscous drag coefficient on a rotary motion of the at least one of the plurality of joints in response to the applied external force is adjusted.

(32)

The surgical imaging apparatus according to (16), wherein the circuitry controls the at least one actuator such that a ratio of the applied external force to a travel distance of the at least one of the plurality of joints in response to the applied external force is adjusted.

(33)

The surgical imaging apparatus according to (32), wherein the circuitry stores at least two different values for the ratio, and switches the value of the ratio between the at least two different values in response to an input.

(34)

The surgical imaging apparatus according to (16), wherein the circuitry controls the at least one actuator such that the video camera moves only on a plane of a cone having a certain point in a space as an apex, and such that a photographing direction of the video camera is fixed on the certain point, in response to an input.

(35)

The surgical imaging apparatus according to (34), wherein a distance between the video camera and the certain point is maintained constant.

(36)

The surgical imaging apparatus according to (35), wherein the certain point is a focus position of the video camera.

(37)

The surgical imaging apparatus according to (16), further comprising a switch disposed at the distal end that receives an input.

(38)

The surgical imaging apparatus according to (16), further comprising at least one display that displays an image captured by the video camera.

(39)

The surgical imaging apparatus according to (38), wherein display size of the display is greater than or equal to 55 inches.

(40)

The surgical imaging apparatus according to (38), wherein the display has a resolution of at least 3840×2160 pixels (4K resolution).

(41)

The surgical imaging apparatus according to (16), wherein the circuitry controls the at least one actuator based on a control value for whole body cooperative control of the multi-link, multi-joint structure.

(42)

The surgical imaging apparatus according to (41), wherein the circuitry calculates the control value according to generalized inverse dynamics using a state of the multi-link structure acquired based on the joint force as detected by the circuitry, a purpose of motion of the a multi-link, multi-joint structure, and a constraint condition of the multi-link, multi-joint structure.

(43)

The surgical imaging apparatus according to (42), wherein the circuitry calculates the control value based on virtual force to achieve the purpose of motion, and actual force obtained by converting the virtual force into force for driving the at least one of the plurality of joints based on the constraint condition.

(44)

The surgical imaging apparatus according to (42), wherein the circuitry controls the at least one actuator based on a command value to achieve an ideal response of the multi-link, multi-joint structure, the command value being calculated by correcting the control value to compensate for influence of a disturbance on at least one of the plurality of joints.

(45)

The surgical imaging apparatus according to (42), wherein the circuitry is configure to control the at least one actuator such that gravity acting on the multi-link, multi-joint structure is negated, and that movement of the multi-link, multi-joint structure in a direction of the applied external force is supported.

(46)

The surgical imaging apparatus according to (16), wherein the circuitry is configured to detect a rotational angle of at least one of the plurality of joints.

(47)

The surgical imaging apparatus according to (16), wherein the circuitry is configured to detect external torque applied to the at least one of the plurality of joints and generated torque generated by the at least one actuator.

(48)

The surgical imaging apparatus according to (16), wherein the video camera is configured to capture an image having a resolution of at least 3840×2160 pixels (4K resolution).

(49)

The surgical imaging apparatus according to (48), wherein the video camera includes a 4K CMOS sensor.

(50)

The surgical imaging apparatus according to (16), wherein the video camera is an endoscope.

(51)

The surgical imaging apparatus according to (16), wherein the multi-link, multi-joint structure has six or more degrees of freedom.

(52)

A surgical video microscope comprising:

a multi-link, multi-joint structure including a plurality of joints that interconnect a plurality of links to provide the multi-link, multi-joint structure with a plurality of degrees of freedom, at least one video camera being disposed on a distal end of the multi-link, multi-joint structure;

at least one actuator that drives at least one of the plurality of joints; and circuitry configured to:

detect a joint force experienced at the at least one of the plurality of joints in response to an applied external force, and control the at least one actuator based on the joint force so as to position the video camera.

(53)

A neurosurgical imaging apparatus comprising:

a multi-link, multi-joint structure including a plurality of joints that interconnect a plurality of links to provide the multi-link, multi-joint structure with a plurality of degrees of freedom, at least one video camera being disposed on a distal end of the multi-link, multi joint structure;

at least one actuator that drives at least one of the plurality of joints; and circuitry configured to:

detect a joint force experienced at the at least one of the plurality of joints in response to an applied external force, and control the at least one actuator based on the joint force so as to position the video camera.

(54)

A surgical imaging apparatus control method comprising:

detecting a joint force experienced at at least one of a plurality of joints of a multi-link, multi-joint structure of the surgical imaging apparatus in response to an applied external force, the plurality of joints interconnecting a plurality of links to provide the multi-link, multi-joint structure with a plurality of degrees of freedom, at least one video camera being disposed on a distal end of the multi-link, multi-joint structure; and controlling, using circuitry, at least one actuator that drives at least one of the plurality of joints based on the joint force so as to position the video camera.

(55)

A non-transitory computer readable medium including executable instructions, which when executed by a computer cause the computer to execute a surgical imaging apparatus control method, the method comprising:

detecting a joint force experienced at at least one of a plurality of joints of a multi-link, multi-joint structure of the surgical imaging apparatus in response to an applied external force, the plurality of joints interconnecting a plurality of links to provide the multi-link, multi-joint structure with a plurality of degrees of freedom, at least one video camera being disposed on a distal end of the multi-link, multi-joint structure; and controlling at least one actuator that drives at least one of the plurality of joints based on the joint force so as to position the video camera.

REFERENCE SIGNS LIST 1 robot arm control system
10 robot arm apparatus
20 control device
30 display device
110 arm control unit
111 drive control unit
120 arm unit
130 joint unit
131 joint driving unit
132 rotational angle detecting unit
133 torque detecting unit
140 imaging unit
210 input unit
220 storage unit
230 control unit
240 whole body cooperative control unit
241 arm state acquiring unit
242 operation condition setting unit
243 virtual force calculating unit
244 actual force calculating unit
250 ideal joint control unit
251 disturbance estimating unit
252 command value calculating unit

The invention claimed is:

1. A surgical imaging system comprising:
a multi-link, multi-joint structure including a plurality of joints that interconnect a plurality of links to provide the multi-link, multi-joint structure with a plurality of degrees of freedom, at least one video camera being disposed on a distal end of the multi-link, multi-joint structure, the at least one video camera configured to capture a three-dimensional (3D), optically magnified image having a resolution of at least 3840×2160 pixels (4K resolution);
at least one actuator that drives at least one of the plurality of joints;
at least one display having a resolution of at least 3840× 2160 pixels (4K resolution) that displays the 3D, optically magnified, 4K resolution image captured by the video camera; and
circuitry configured to:
control the at least one actuator such that a motion of the multi-link, multi-joint structure enables the video camera to maintain aim at a point, which is away from the video camera by a focal length, during movement of the video camera, and
control the video camera to autofocus the 3D, optically magnified, 4K resolution image captured by the video camera aimed at the point.

2. The surgical imaging system according to claim 1, wherein the circuitry is further configured to control the at least one actuator to move the video camera in a direction of an applied external force.

3. The surgical imaging system according to claim 1, wherein the circuitry is further configured to control the at least one actuator to move the video camera such that a field of view of the video camera is adjusted.

4. The surgical imaging system according to claim 1, wherein the circuitry is further configured to control a movement speed of the video camera based on a magnitude of an applied external force.

5. The surgical imaging system according to claim 1, wherein the circuitry is further configured to control the video camera to autofocus during a movement of the video camera.

6. The surgical imaging system according to claim 1, further comprising at least one sensor that detects a joint force, the sensor being disposed at the at least one of the plurality of joints,
wherein the circuitry is further configured to detect the joint force based on a signal output by the at least one sensor.

7. The surgical imaging system according to claim 1, wherein the circuitry is further configured to digitally magnify and reduce the 3D image.

8. The surgical imaging system according to claim 1, wherein the circuitry is further configured to control the video camera to optically magnify and reduce the 3D image.

9. The surgical imaging system according to claim 1, wherein the circuitry is further configured to control the at least one actuator such that a position of the video camera is stabilized.

10. The surgical imaging system according to claim 9, wherein the circuitry is further configured to control the at least one actuator to deactivate the video camera stabilization in response to an input.

11. The surgical imaging system according to claim 1, wherein the circuitry is further configured to control the at least one actuator such that a viscous drag coefficient on a rotary motion of the at least one of the plurality of joints in response to an applied external force is adjusted.

12. The surgical imaging system according to claim 1, wherein the circuitry is further configured to control the at least one actuator such that a ratio of an applied external force to a travel distance of the at least one of the plurality of joints in response to the applied external force is adjusted.

13. The surgical imaging system according to claim 12, wherein the circuitry is further configured to store at least two different values for the ratio, and switch the value of the ratio between the at least two different values in response to an input.

14. The surgical imaging system according to claim 1, wherein the circuitry is further configured to control the at least one actuator such that the video camera moves only on a plane of a cone having a certain point in a space as an apex, and such that a photographing direction of the video camera is fixed on the certain point, in response to an input.

15. The surgical imaging system according to claim 14, wherein a distance between the video camera and the certain point is maintained constant.

16. The surgical imaging system according to claim 15, wherein the certain point is a focus position of the video camera.

17. The surgical imaging system according to claim 1, further comprising a switch disposed at the distal end that receives an input.

18. The surgical imaging system according to claim 1, wherein display size of the display is greater than or equal to 55 inches.

19. The surgical imaging system according to claim 1, wherein the circuitry is further configured to control the at least one actuator based on a control value for whole body cooperative control of the multi-link, multi joint structure.

20. The surgical imaging system according to claim 19, wherein the circuitry is further configured to calculate the control value according to generalized inverse dynamics using a state of the multi-link structure acquired based on a joint force as detected by the circuitry, the purpose of motion of the a multi-link, multi-joint structure, and a constraint condition of the multi-link, multi-joint structure.

21. The surgical imaging system according to claim 20, wherein the circuitry is further configured to calculate the control value based on a virtual force to achieve the purpose of motion, and an actual force obtained by converting the virtual force into force for driving the at least one of the plurality of joints based on the constraint condition.

22. The surgical imaging system according to claim 20, wherein the circuitry controls the at least one actuator based on a command value to achieve an ideal response of the multi-link, multi joint structure, the command value being calculated by correcting the control value to compensate for influence of a disturbance on at least one of the plurality of joints.

23. The surgical imaging system according to claim 20, wherein the circuitry is configured to control the at least one actuator such that gravity acting on the multi-link, multi-joint structure is negated, and that movement of the multi-link, multi-joint structure in a direction of an applied external force is supported.

24. The surgical imaging system according to claim 1, wherein the circuitry is configured to detect a rotational angle of at least one of the plurality of joints.

25. The surgical imaging system according to claim 1, wherein the circuitry is configured to detect external torque applied to the at least one of the plurality of joints and generated torque generated by the at least one actuator.

26. The surgical imaging system according to claim 1, wherein the video camera includes a 4K CMOS sensor.

27. The surgical imaging system according to claim 1, wherein the video camera is an endoscope.

28. The surgical imaging system according to claim 1, wherein the multi-link, multi-joint structure has six or more degrees of freedom.

29. The surgical imaging system according to claim 1, wherein the movement of the video camera is movement within a surface of a cone having a same part as an apex, and an axis of the cone is used as a pivot axis in a state in which a photographing direction of the video camera is fixed to the same part.

30. The surgical imaging system according to claim 1, wherein the focus is maintained even when the distance between an object in focus and the video camera is changed.

31. The surgical imaging system according to claim 1, wherein the circuitry is configured to control the at least one actuator such that the video camera continues to photograph a same part even after movement of the video camera with respect to an object in focus such that the object in focus remains within a frame of the at least one display.

32. The surgical imaging system according to claim 1, wherein a locked distance and the point on a same part are set to a focal length and a focal point of the video camera respectively.

\* \* \* \* \*